(12) United States Patent
Wessels Wells et al.

(10) Patent No.: US 11,494,910 B1
(45) Date of Patent: Nov. 8, 2022

(54) EMBRYO VIABILITY EVALUATION USING AI/ML ANALYSIS OF SHORT DURATION VIDEO

(71) Applicant: Emgenisys, Inc., Houston, TX (US)

(72) Inventors: Cara Elizabeth Wessels Wells, Dripping Springs, TX (US); Russell Killingsworth, Shamrock, TX (US)

(73) Assignee: Emgenisys, Inc., Houston, TX (US)

( * ) Notice: Subject to any disclaimer, the term of this patent is extended or adjusted under 35 U.S.C. 154(b) by 0 days.

(21) Appl. No.: 17/872,707

(22) Filed: Jul. 25, 2022

Related U.S. Application Data

(63) Continuation of application No. 17/688,109, filed on Mar. 7, 2022, now Pat. No. 11,455,725, which is a
(Continued)

(51) Int. Cl.
*G06K 9/00* (2022.01)
*G06T 7/00* (2017.01)
(Continued)

(52) U.S. Cl.
CPC ............. *G06T 7/0012* (2013.01); *G06N 3/02* (2013.01); *G06T 3/40* (2013.01); *G06T 7/20* (2013.01); *G16H 30/20* (2018.01); *G16H 30/40* (2018.01); *G16H 50/20* (2018.01); *G16H 50/30* (2018.01); *H04N 5/77* (2013.01);
(Continued)

(58) Field of Classification Search
CPC .......... G06T 7/0012; G06T 3/40; G06T 7/20; G06T 2207/10016; G06T 2207/10056; G06T 2207/20076; G06T 2207/20081; G06T 2207/20084; G06T 2207/30044;
(Continued)

(56) References Cited

U.S. PATENT DOCUMENTS

| 9,177,192 B2 | 11/2015 | Wang et al. |
| 9,710,696 B2 | 7/2017 | Wang et al. |

(Continued)

FOREIGN PATENT DOCUMENTS

| WO | 2019060911 A1 | 3/2019 |
| WO | 2019191682 A1 | 10/2019 |

(Continued)

OTHER PUBLICATIONS

International Search Report and Written Opinion; PCT Application No. PCT/US2021/044423; dated Nov. 16, 2021.
(Continued)

*Primary Examiner* — Jonathan S Lee
(74) *Attorney, Agent, or Firm* — Novak Druce Carroll LLP

(57) ABSTRACT

A computer-implemented system and method for predicting an embryo outcome by processing video image data of the embryo. The method includes receiving image data derived from video of a target embryo taken at substantially real-time frame speed during an embryo observation period of time. The video contains recorded morphokinetic movement of the target embryo occurring during the embryo observation period of time. The movement is represented in the received image data and the received image data is processed using a model generated utilizing machine learning and correlated embryo outcome data.

30 Claims, 11 Drawing Sheets

Related U.S. Application Data continuation of application No. 17/687,368, filed on Mar. 4, 2022, and a continuation of application No. 17/687,265, filed on Mar. 4, 2022, and a continuation of application No. 17/687,437, filed on Mar. 4, 2022, and a continuation of application No. 17/687,319, filed on Mar. 4, 2022, and a continuation of application No. 17/687,416, filed on Mar. 4, 2022, and a continuation of application No. PCT/US2021/044423, filed on Aug. 3, 2021.

(60) Provisional application No. 63/060,554, filed on Aug. 3, 2020.

(51) Int. Cl.
| | |
|---|---|
| *G06T 3/40* | (2006.01) |
| *G06T 7/20* | (2017.01) |
| *G06N 3/02* | (2006.01) |
| *G16H 30/20* | (2018.01) |
| *G16H 50/20* | (2018.01) |
| *H04N 5/77* | (2006.01) |
| *G16H 50/30* | (2018.01) |
| *G16H 30/40* | (2018.01) |

(52) U.S. Cl.
CPC ............ *G06T 2207/10016* (2013.01); *G06T 2207/10056* (2013.01); *G06T 2207/20076* (2013.01); *G06T 2207/20081* (2013.01); *G06T 2207/20084* (2013.01); *G06T 2207/30044* (2013.01)

(58) Field of Classification Search
CPC .......... G06N 3/02; G16H 30/20; G16H 30/40; G16H 50/20; G16H 50/30; H04N 5/77

USPC ........................................................ 382/128
See application file for complete search history.

(56) References Cited

U.S. PATENT DOCUMENTS

| | | |
|---|---|---|
| 10,942,170 B2 | 3/2021 | Tan et al. |
| 11,169,064 B2 | 11/2021 | Prien et al. |
| 2014/0087415 A1 | 3/2014 | Ramsing et al. |
| 2015/0268227 A1 | 9/2015 | Tan et al. |
| 2016/0078272 A1 | 3/2016 | Wang et al. |
| 2018/0256304 A1 | 9/2018 | Sheena |
| 2019/0024030 A1 | 1/2019 | Wells et al. |
| 2020/0011883 A1 | 1/2020 | Beim et al. |
| 2020/0311916 A1 | 10/2020 | Tran |
| 2021/0249135 A1 | 8/2021 | Rimestad et al. |
| 2022/0012873 A1 | 1/2022 | Silver et al. |
| 2022/0198657 A1* | 6/2022 | Hall .................. G06N 3/08 |

FOREIGN PATENT DOCUMENTS

| | | |
|---|---|---|
| WO | 2021148961 A1 | 7/2021 |
| WO | 2022031765 A1 | 2/2022 |

OTHER PUBLICATIONS

Kanakasabapathy, Manoj Kumar et al., "Development and Evolution of Inexpensive Automated Deep Learning-Based Imaging Systems for Embryology", Lab Chip 19(24) (2019): 4139-4145; Dec. 21, 2019.

Siva-Rodriguez, Julio et al., "Predicting the Success of Blastocyst Implantation from Morphokinetic Parameters Estimated through CNNs and Sum of Absolute Differences", 2019 27th European Signal Processing Conference (EUSIPCO); IEEE, 2019. (Year: 2019).

* cited by examiner

EMBRYO VIABILITY EVALUATION USING AI/ML ANALYSIS OF SHORT DURATION VIDEO

CROSS REFERENCE TO RELATED APPLICATIONS

The present patent application is a continuation patent application of U.S. application Ser. No. 17/688,109 filed Mar. 7, 2022, which is a continuation patent application of each of the following patent applications:

(a) U.S. application Ser. No. 17/687,265 filed Mar. 4, 2022, which is a continuation application of PCT/US2021/044423 filed Aug. 3, 2021, designating the United States and which claims the benefit of U.S. Provisional Patent Application No. 63/060,554, filed Aug. 3, 2020;

(b) U.S. application Ser. No. 17/687,319 filed Mar. 4, 2022, which is a continuation application of PCT/US2021/044423 filed Aug. 3, 2021, designating the United States and which claims the benefit of U.S. Provisional Patent Application No. 63/060,554, filed Aug. 3, 2020;

(c) U.S. application Ser. No. 17/687,368 filed Mar. 4, 2022, which is a continuation application of PCT/US2021/044423 filed Aug. 3, 2021, designating the United States and which claims the benefit of U.S. Provisional Patent Application No. 63/060,554, filed Aug. 3, 2020;

(d) U.S. application Ser. No. 17/687,416 filed Mar. 4, 2022, which is a continuation application of PCT/US2021/044423 filed Aug. 3, 2021, designating the United States and which claims the benefit of U.S. Provisional Patent Application No. 63/060,554, filed Aug. 3, 2020;

(e) U.S. application Ser. No. 17/687,437 filed Mar. 4, 2022, which is a continuation application of PCT/US2021/044423 filed Aug. 3, 2021, designating the United States and which claims the benefit of U.S. Provisional Patent Application No. 63/060,554, filed Aug. 3, 2020; and (f) International Patent Application No. PCT/US2021/044423 filed Aug. 3, 2021, designating the United States and which claims the benefit of U.S. Provisional Patent Application No. 63/060,554, filed Aug. 3, 2020.

Each of the aforementioned patent applications is expressly incorporated herein by reference, in its entirety, without disclaimer.

SUMMARY

Combining state-of-the-art artificial intelligence (AI), machine learning (ML), video image data processing and optics systems, practical insights from clinical embryologists and scientific input from data engineers, the present technology provides the world's most comprehensive embryo evaluation system for detecting and/or predicting embryo morphokinetics, viability and developmental potential in a single, easy to use system. The technology processes digital video image data from real-time video taken of an embryo proximate in time before transfer or storage such as by cryopreservation. The image data of the resulting signal is then processed to reveal information, heretofore hidden, to the operator and other interested parties. With this technology, model-processed real-time video image data of an embryo can predict, among other things: (1) the embryo's present viability at time of transfer, (2) the embryo's inviability at time of planned transfer, (3) the embryo's likelihood (qualitatively, quantitative and/or probabilistic) to result in pregnancy and produce live offspring, (4) the embryo's likelihood of producing a male offspring, (5) the embryo's likelihood of producing a female offspring, (6) genetic inferiority (likelihood to embody disease or genetic issue, and of what type) of the embryo and (7) genetic superiority (likelihood to produce desired traits in offspring) of the embryo. The instant deep learning model(s) can also rank a number (group) of embryos based on one or more predictive embryo characteristics or predicted offspring traits based on generated relative strengths (probability of occurrence) of the predicted characteristic among the group of blastocysts enabling an embryologist's selection and transfer of the most desirable embryos into recipient(s).

In one embodiment, video image data is utilized to develop deep learning models that provide the basis for an AI/ML-based software package that enables a non-invasive, quantitative, non-subjective system and method to identify high-quality, viable embryos likely to result in pregnancy and healthy offspring as exemplified in FIG. 1 of the accompanying drawings. Currently, embryologists have limited ability to evaluate embryo health and viability, making it all too common to unknowingly transfer dead or otherwise inviable embryos into recipients. The present technology allows a user to make more informed decisions about which embryo(s) to transfer and reduces the transfer of low-quality embryos which will not establish pregnancy. Technologies such as this that improve pregnancy outcomes of IVF beneficially affect patients both physically and psychologically, as well as having a positive financial impact on the industry as a whole through cost reduction. Another aim of this technology is to enhance the workflow of the user by enabling a single multi-embryo video/scan to provide immediate feedback through real time image data collection and processing. In the case of animal breeding and production, the technology is utilized to select the highest quality embryos that are most likely to achieve pregnancy and produce disease-free offspring that embody the most superior of desired traits, including sex.

DETAILED DESCRIPTION

Figure 1:
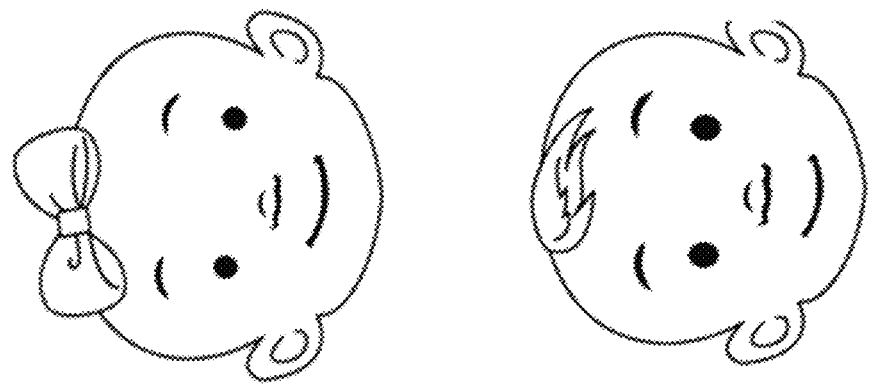
FIG. 1 represents a goal of the presently disclosed technology which is, among others, predicting an embryo's competence to establish pregnancy and produce the live birth of a desired offspring as herein described.

Users of the presently disclosed technology include reproductive endocrinologists, specialized OB/GYN's, embryologists, veterinarians, animal breeders and trained laboratory personnel, among others. In the realm of human reproduction, users of this technology include embryology lab directors and clinical embryologists who are practicing Assisted Reproductive Techniques (ART). ART patients, and in particular IVF (In Vitro Fertilization) patients, are prime influencers of this technology as they play a key role in selecting which fertility treatment(s) to employ that best assures a live birth out of their scarce and fragile inventory of gametes/oocytes/embryos. As a precursor to this technology's development, customer interviews were conducted with 231 interviewees during the 2018 National Science Foundation I-Corps National Atlanta Winter Cohort regarding needs in the industry. Based on the results of those interviews, the perspective became clear that there have not been any transformative technologies to predict embryo viability in nearly four decades.

In practice, clinical embryologists and/or otherwise trained personnel are responsible for selecting the embryo to be transferred into the recipient and that responsible person often unknowingly selects and transfers non-viable embryo(s) into the recipient due to lack of accurate means to evaluate embryo health and quality. Embryologists' and fertility clinics' reputations are predominantly based on published pregnancy success rates, so there is active competition for the highest rankings, as high rankings best produce revenue. Poised for success, this technology is in a class of its own as the only embryo assessment tool that is NOT subjective (non-subjective), NOT invasive (non-invasive) and enables real-time assessment of presently existing embryo morphokinetics in both human and non-human mammals.

Infertility in humans is classified as a disease by the World Health Organization and affects 48.5 million couples worldwide. In Vitro Fertilization is presently the most effective treatment of infertility, but the produced livebirth rate in 2018 was only 26%. Unfortunately, IVF is renowned for being expensive, stressful and generally unsuccessful, and which more often than not, delivers a disappointing experience.

On the positive side however, ART is expanding the relevant market as it is no longer just a treatment of infertility but has the added the capability to extend fertility to others in many different situations though cryopreservation of eggs, sperm and embryos. One example is the preservation of healthy cells/gametes of cancer patients prior to undergoing chemotherapy in the event the patient is not able to produce them after such treatment. ART also enables single individuals and homosexual couples to enjoy biological families, which might otherwise not have been possible. For these reasons, as well as others, ART is becoming a routine method to start or extend a family, but improvements are definitely welcome.

Since the birth of Louise Brown in 1978 by IVF, over 10 million babies have been born via IVF and Intracytoplasmic Sperm Injection (ICSI), worldwide. In the United States, babies born from IVF/ICSI comprise nearly 2% of the annual birth count. For IVF, a woman is given superovulatory hormones to encourage more eggs to develop in the ovaries at once. The woman's follicular development is closely monitored to time the egg retrieval in which the fertility specialist aspirates the eggs from the ovary. Each egg is fertilized with sperm and the fertilized eggs are permitted to develop into embryos over the course of five to six days. It is likely that multiple embryos will develop into seemingly healthy blastocysts. From them, the embryologist is responsible for choosing which embryo(s) to transfer into the patient. Any remaining embryos are typically frozen and can be used for subsequent transfer attempts. This process is referred to as a "round" of IVF and generally costs about $23,000. If a child is not produced in this first round, the patient can opt to undergo a frozen transfer, in which one or more of the remaining frozen embryos is thawed and transferred into the patient. Frozen embryos can be transferred until no more are available, in which case the entire process must start over. On average, patients undergo 2.7 rounds of IVF and spend $60,000 to achieve a pregnancy that survives to term. Unfortunately, a major contributor to the low success rate of IVF is an inability to discern and choose healthy, viable embryos at the time of transfer.

There are approximately 450 IVF clinics in the United States, as well as donor egg banks that collaborate with over 150 of the IVF clinics. Out of those clinics, 271,398 human embryo transfer procedures were performed in 2018. Approximately 50% of those IVF procedures in women ages 35 and under resulted in a live birth. For women ages 42 and older, the number plumets to 3.9% of egg transfers that result in a birth. With that as background, it is clear that any technology that enables embryologists to select embryos most likely to produce a healthy birth and/or survive and thrive after cryopreservation has great prospect for adoption by the industry. Just considering human embryo transfers in the United States (excluding animal transfers), it is calculated that a 3% improvement in pregnancy outcomes would currently provide over $187,000,000 in annual patient savings. Additionally, technologies like this that improve pregnancy success on a per-transferred-embryo basis lessens the need to transfer multiple embryos into a single recipient which reduces the risk of undesired, multiple births. This clearly reduces costs, but equally important, it reduces complications to mothers and babies from simultaneous gestations.

Embryo screening is limited by the requirement that embryos must survive the diagnostic process, unharmed. Many existing assessment methods such as staining and electron microscopy are only used in a research setting because the processes are lethal. The most commonly used method to assess the quality of embryos and oocytes for transfer is a morphological analysis using a light microscope. In this assessment, the technician examines the cells for visually apparent characteristics such as cell shape, size, symmetry and color. While this method is noninvasive and cost effective, it is subjective, relying solely on the examiner's discretion and does not include information about an embryo's biochemical content or genetic make-up. As an aid to morphological analysis, time lapse imaging systems, such as the EmbryoScope®, are available that link developmental events with the elapsed time at which the different events occur. However, in a recent report published in the Journal of Reproduction and Genetics, only 17% of surveyed labs had a time lapse imagining system. Moreover, a majority of surveyed lab directors responded that "time lapse imaging will not become the standard of care because the technology is too expensive, there is no evidence it provides additional benefit and it is too time intensive and impractical."

Today, genetic assessment requires a biopsy of cells from the embryo. The biopsied cells are sent to an off-site lab for genetic testing and the left-behind embryo must be frozen until lab results are received. Pre-implantation Genetic Testing (PGT) encompasses both pre-implantation genetic screening and pre-implantation genetic diagnosis, which can inform embryologists and patients of genetic abnormalities (such as aneuploidy or trisomy), genetic disease and embryo sex. PGT was designed for high-risk patients with a known condition or genetic trait, and not for the average IVF/ART patient. Disadvantages of PGT are its invasive nature, increased risk of cell death and it requires expensive equipment and highly trained personnel. The costs range from $4000-$7500, which are in addition to the base fees associated with IVF procedures. PGT data suggests there is no difference in pregnancy rate for patients under the age of 36 years old. Other reports claim PGT significantly increases pregnancy outcomes, but many physicians warn that it also increases the incidence of miscarriage, which indicates that the "take home baby rate" is likely unimproved. In contrast, the presently disclosed non-invasive embryo analysis system provides a newly-available superior standard of care, easily incorporated into current laboratory protocols and procedures.

The solutions made possible by the present technology will quickly penetrate the $6.2 billion US market of the human clinical infertility sector. It also easily scales to service the $37.7 billion global infertility market. With fewer than half of the people suffering from infertility seeking care, technologies such as the present that reduce cost and increase success rates will undoubtedly expand and grow the already substantial infertility care market. As an example, one published market analysis indicates that a 50% reduction in the price of IVF services would translate into a 160% increase in the utilization of fertility services.

Turning now from the human experience to the animal sciences, it is noted that the global population is expected to reach 9.5 billion by 2050, an approximately 20% increase over 2020. It is projected that the demand for animal derived protein will at least double, resulting in concerns over food security and sustainability. Current agricultural practices are already placing tremendous pressure on the earth's finite resources and are largely responsible for a vast proportion of greenhouse gas (GHG) emissions. Well managed cattle (also referred to herein as cows and/or bovine) production helps to meet food security and environmental goals, as beef and dairy products both provide nutrient-rich, high-quality protein to consumers. Cattle are particularly suited to meat production as they are a robust animal that adapt well to changes in climate and can graze on pastureland generally not suitable for crop production due to climate, soil and topographic limitations. Cows convert forage into high quality protein and excrete fertilizer as a beneficial by-product. Modern cattle production practices have been adapted to reduce the industry's carbon footprint and as a result methane output has declined approximately 40% since 1980. Genetic selection through progressive breeding strategies can further reduce GHG emissions from cattle production by improving animal efficiency, improving the feed conversion ratio, reducing dry matter intake and reducing enteric methane production. Selection for genetic superiority in cattle, among other animals, is enabled by the presently disclosed technology in which an appropriately trained AI/ML model(s) predicts the likelihood that a particular embryo will produce offspring having desired characteristic(s) based on processing digital video image data extracted from a real-time, short duration video typically taken right before transfer or storage (cryopreservation) of the embryo.

As stated above, methane ($CH_4$) is the major green-house gas emitted by ruminant production systems with $CH_4$ from enteric fermentation accounting for 12% to 17% of that emission. Diet is a major factor (roughage and concentrate) contributing to methane emissions from ruminants. Dietary aspects known to reduce ruminant methane production include decreasing the proportion of cereal grains and legumes in the animals' diets and adding plant species that contain secondary metabolites such as tannins and saponins which affect methanogenesis in the rumen and reduce ruminant methane emissions. Effectiveness of feedlot programs implementing dietary improvements has improved the carbon footprint of beef production in Canada to as low as 17 kg of carbon dioxide equivalents ($CO_2e$) per kg of food for feedlot finished beef as compared to grass-finished beef in Brazil that emit as much as 40 kg $CO_2e$ per kg of food. Despite the known advantages of certain plants, grassland renovation is often not practical as many of these plant species are weak competitors compared to native grasses and consequently is all-too-often not affordable or sustainable. Therefore, the most practical and rapid mitigation procedure is to reduce the per cow $CH_4$ emission through animal breeding and genetic selection for feed efficiency, as those effects are permanent and cumulative.

Genetic selection utilizing the present technology can reduce GHG emissions from beef and dairy cattle production systems because it: (1) enables increased production per animal which reduces the number of individual animals to produce the same amount of beef and dairy; (2) lowers emissions per unit of beef or dairy produced; and (3) reduces consumption of grain, concentrates, roughage, water and land. Embryo transfer and in vitro fertilization can further perpetuate genetic traits of superior animals because they enable genetically superior animals to produce more offspring in a single year than can be achieved in nature. Additionally, ART can help producers control the sex ratio to be favorable for the most desired sex for the operation. As an example, dairies have a preference for female cows because they produce milk and males do not. Potentiated bovine embryo transfer provides other economic advantages such as decreased calving intervals, more consistent calf crop production and maximized product value. Due to these benefits, ET and IVF have become routine breeding strategies in livestock operations and approximately 2.5 million cattle embryos are transferred in North America each year.

To perform ET or IVF currently, superior female animals referred to as "donors" are stimulated with superovulatory hormones to produce an increased number of oocytes. The oocytes can be aspirated from the ovary by a veterinarian and fertilized in vitro or the animal can be artificially inseminated and fertilized embryos can be flushed from the uterus six to seven days later. Today, the veterinarian or embryologist examines the embryos under a light microscope and assigns a grade based on visible morphological characteristics. Highly graded, grade-1 and grade-2 embryos are transferred into recipients or frozen for use at a later date.

Unfortunately, the success rates of ET and IVF in cattle are still very low. The success rate (pregnancy achieved) of ET today is less than 65% in cattle, and the success rate of conventional IVF is less than 30% in cattle. While causes of failed pregnancy are multi-factorial and can stem from embryonic, maternal and/or environmental stressors, it is estimated that 20% of transferred embryos are actually non-viable at the time of transfer and will never result in pregnancy.

Technology that could increase pregnancy rates and optionally control sex ratio would be extremely valuable. For cattle, approximately $1200 is invested into each embryo transferred, regardless of whether it establishes a pregnancy or produces a calf of desired sex. With current pregnancy outcomes at less than 65% for conventional embryo transfer and less than 30% for IVF, technology such as that presently disclosed that improves pregnancy outcomes and provides significant savings to producers will be quickly adopted. Additionally, enabled selection for genetic superiority and desired sex adds further value. ET coupled with the use of the present technology is the fastest way to change and improve the genetics in a herd and maximize beef producer and dairy profitability.

The presently disclosed technology facilitates the provision of a comprehensive, portable platform for obtaining, on-site, real-time embryo video clip(s), and while still on-site, processing the obtained video image data using an appropriately trained AI/ML model to make relevant predictions about a target embryo(s) and/or offspring produced therefrom.

Aspects of the present technology that provide a competitive advantage include: (1) its non-invasive nature, (2) it is not subjective, (3) it utilizes quantitative analysis that incorporates artificial intelligence and deep learning algorithms, (4) it evaluates and/or predicts embryo growth, health, sex and many other embryo characteristics and/or traits of offspring produced therefrom by processing image data from real-time video and provides immediate diagnostic feedback (in minutes, if not seconds) to the user at an affordable price. This technology subjects the target embryo to essentially no additional risk, does not require biopsy or manipulation of cells and facilities the evaluation of multiple embryos at one time resulting in predictive data being available for each embryo in minutes, if not less. In an alternate configuration, the presently disclosed technology enables the user to "see" changes in embryo morphokinetics within the same time frame, if the diagnostic image data is optionally processed for magnification/amplification as herein described.

At different times, real-time video image data has been collected from anywhere between 150 and 1000 bovine embryos for any one study. Real-time digital video image data is collected and processed from the bovine embryos, together with correlated pregnancy and/or offspring characteristic/trait data (correlated outcome data). The video from which the real-time video image data is derived must contain a video resolution sufficient to record morphokinetic movement of the target embryo. From the video image data, changes in embryo morphokinetics are observed in substantially real time. Another characteristic of the target embryo evidenced in the received image data is elasticity of the embryo's outer wall. Utilizing the correlated outcome data for model training, predictive model(s) have been generated regarding produced pregnancy and offspring outcomes.

According to this disclosure, the origin of the digital video image data used for both AI/ML model training and predictive processing is real-time video taken of pre-implantation embryos that are typically in the blastocyst or morula stage of development, and which occurs between about five to nine days, post fertilization. The embryos can be the product of either in vitro (outside the donor) fertilization ("IVF") or in vivo (within the donor) fertilization by artificial insemination. In the case of in vivo fertilization, the produced embryos are subsequently flushed from the host, typically for transfer into multiple individual recipients. In this specification, references to "embryo" include at least blastocyst and morula stage embryos and, vice versa, regardless of the embryo being the product of in vitro or in vivo fertilization.

For taking the referenced video(s), one or more embryos are placed in a disposable, typically polystyrene container (dish) compatible with the employed video image and diagnostic equipment. Advantageously, such receiving dish can have a unique QR code compatible with the analytic software for embryo identification. In one configuration, the dish can comprise (include, but not be limited to) a plurality of pre-labeled wells, each intended to receive one embryo, and which among other things: (1) aids proper placement of the embryos in the technician's and/or camera's field of view, (2) provides an identify to each of several contained embryos, and (3) correlates generated predictions to the respective embryos.

The real-time digital video clip(s) can be taken with a variety of video imaging equipment including, among others, digital cameras, action cameras, smartphone cameras, tablet cameras, board cameras and the like. In the instance of board cameras, also called printed circuit board (PCB) cameras, the included optical devices and image sensors are mounted directly on a circuit board, as is often the case in smartphones. An associated display can be optionally provided to a board camera, as is the case with a smartphone, and the image signals are relayed through an I/O of the PCB. As there are no analog controls, recording options are also controlled through the interface.

It is desirable that each real-time video clip comprising image data used as training data (and subsequently, video-based target image data to be analyzed using resulting so-trained models) be relatively short. For example, the video clips advantageously extend from around fifteen seconds up to several minutes long in duration. It is not necessary that each clip be individually recorded. Multiple short duration clips can be excised out of a longer blastocyst video. The duration of the training clip is selected to correlate best to video image data that will be processed by the resulting model; therefore, utilizing training data source clips of similar duration subsequently enables more accurate predictions from the generated model.

Using appropriately trained model(s), assessment is made of a blastocyst's movement recorded in one of these video clips of relatively short duration. The duration of the video clip is preferably 30 seconds or less (5, 10, 15, 20, 25, 30 seconds), but the duration of the clip can be as much as one minute, two minutes, 5 minutes or more, though such longer clips are less desirable given their increased amount of constituent data. Video described in this disclosure is referred to as real-time video, as compared to time-lapse video that is historically known for use in embryo evaluation and assessment. Time-lapse "video" is made-up of a series of consecutive still photos or "frames" that have substantial time-spacing (30 seconds or more, but typically minutes or hours) therebetween. Heretofore, relatively short duration, real-time video recordings of embryos have not been analyzed regarding existing embryo short, rapid morphokinetic movement because none was visibly detectable, even under typically employed microscope magnification.

In fact, as described herein, significant morphokinetic movement has been revealed to be occurring in observed blastocysts over the short video time periods. In accordance with the present disclosure, this movement is recorded using real-time video taken via a microscope at a magnification power (e.g., 150×) heretofore accepted as only being suitable for observing a "static" embryo (i.e., a "snap-shot view"). This was a reasonable deduction because technician-observation of a blastocyst under microscope magnification for the same amount of time as video is now taken does not reveal the morphokinetic movement that is occurring because even under microscope magnification, that movement is still humanly imperceptible. Now knowing that the blastocyst's morphokinetic movement is recorded in the image data of these real-time videos as described herein, even though not perceptible, the image data is suitable for model training and/or predictive processing using generated model(s).

The presently described real-time video clips each comprise a series of consecutive, equal time-spaced digital image frames, and the duration of the time spacing is referred to as frame speed. A recorded blastocyst morphokinetic movement traverses a short distance, at a fast rate, and therefore has a commensurately short duration. Consequently, the frame speed utilized for the recordings should be of similar duration, and preferably faster. Exemplarily, frame speeds of ten frames-per-second (10 fps) and fifteen frames-per-second (15 fps) have been utilized to capture blastocyst movement. In practice, faster frame speeds have proven beneficial, particularly in training stages of the presently disclosed AI/ML analysis because the quick, short-distance morphokinetic movements made by the blastocyst are captured with greater accuracy, clarity and fidelity when faster frame speeds are used. Conversely, as video frame speed decreases and there is a greater time gap between consecutive frames, the blastocyst movement becomes less perceptible. At spacings greater than about two frames per second (2 fps), individual morphokinetic movements of the blastocyst can become unobservable. When the duration of a morphokinetic movement is less then the frame speed, that movement can be "lost" in the gap-space between two frames that "straddle" that movement, especially if the movement is a rebounding motion that at first occurs in one direction, and then elastically "snaps back," all within the gap-space between two straddling frames.

Whether being prepared as training data or as target data to be analyzed using generated model(s), preprocessing of the blastocyst image data can advantageously include normalizing the "raw" image data to that of a "standard," comparable blastocyst. Though various known methods can be used to accomplish such normalization of video image data, here, the desired end result is to make each "image" of each blastocyst comparable to one another, with minimized "noise" caused by different setups used to take the various original videos. One example is to adjust each "image" of each blastocyst to the same "size" by scaling up (expanding) or scaling down (shrinking) the respective images to a "standard size."

In some instances, the view area of the videos is normalized to be the same, but not the size of each blastocyst image. This type of normalization is used when relative size drives a predictable outcome. For instance, relative size can be predictive of blastocyst viability and sex. Relatedly, relative blastocyst size can also be a determinative or desirable differentiating factor amongst a group of co-fertilized blastocysts (multiple eggs fertilized at the same time and grown for the same time period) that are being model-assessed for viability and/or sex, and relative size is predictive, or can at least be used to rank the blastocysts for certain predictable pregnancy characteristics and/or offspring traits amongst the group of embryos.

During the training process, a model can be trained to predict among other things about the embryo: viability, likelihood to produce pregnancy, likelihood to result in a live birth, offspring sex probability (how likely to produce a male offspring or how likely to produce a female offspring), and the presence or absence of genetic anomalies and disease, such as diabetes, cancer, other cell growth and the like or the capability for passing along desired characteristic(s) to offspring, such as highly efficient feed utilization.

As an adjunct, embryo video image data processing has been employed in accordance with the present disclosure to observe and evaluate embryo movement responsive to an induced environmental stressor and determined that the observed motion is predictive of related outcomes (good/bad) that are embodied in resulting embryos and/or offspring. This can be useful to determine early prognosis of cancer, metabolic profile, genetic defects and the like. Studying embryo homeostasis mechanisms by enabling visualization and/or other analysis of embryo response (typically movement) to environmental changes has been determined to be useful to optimize culture systems, media, materials, nutrients, and to evaluate cellular metabolites, ambient environment impacts (light, temperature, pressure and the like) and overall developmental competency. Relatedly, the development/testing of vaccines have been aided by the present technology. It has been noted that embryos experience predictive morphokinetic motion when inoculated with certain pathogens. It has also been observed that pathogen-carrying embryos (infected, but otherwise unaffected) experience predictive morphokinetic motion when exposed to vaccines, typically being tested for efficacy against the carried pathogen.

As an example of that described above, it is known that cystic fibrosis (CF) is caused by a genetic mutation in the CF Transmembrane Conductance Regulator gene (CFTR gene) that regulates the movement of chloride in the body. Prospective parents can be screened to determine their carrier status, but the only way to determine whether the genetic mutation has been passed along to an embryo is through pre-implantation genetic diagnosis via biopsy. The expression of CF is an inability to regulate salt and water transport across epithelial tissue. In accordance with the teachings of the present disclosure, processed embryo video image data revealed that embryos embodying the CF genetic mutation experienced detectible reactive motion when exposed to chloride. In this case, clinical exposure was created by adding chloride-containing material (salt) to the liquid media containing the embryo. When an embryo carried the CFTR gene mutation, the addition of chloride stressed the embryo and caused responsive observable motion. In accordance with instant teachings, an appropriately trained model was used to process digital image data from video taken of the potentially affected embryo and predicted whether the CFTR gene mutation was present. The prediction was made in terms of the likelihood (probability) that a resulting offspring would suffer cystic fibrosis. Conversely, the videos of embryos that "tolerated" the addition of chloride to their containing media showed much less reactionary motion. The video image data of that motion was processed using the trained model and a likelihood was predicted that resulting offspring would not embody the CF genetic mutation. In summary, AI/ML models generated according to the teachings of the present disclosure have been demonstrated to competently process digital image data sourced from video taken of embryos responding to an induced stimuli indicative of the presence of a gene mutation in an embryo and predict the likelihood resulting offspring will embody the mutation.

The protocol and process for predicting the presence of most genetic and metabolic diseases embodied in an embryo, and the likelihood of its expression in resulting offspring, follows that which is described above for cystic fibrosis. For example, reactionary motion by an embryo to glucose added to the containing media predicts diabetes, while potassium predicts Hyperkalemic Periodic Paralysis in horses, among others.

As intimated above, the present technology facilitates non-invasive embryo sex selection. There is scientific evidence indicating that male embryos develop faster than female embryos. This is observed by total cell count at the blastocyst stage of development. The data is predominantly anecdotal because it is difficult to count cells non-invasively without harming the embryo. However, for there to be greater male cell count over a predetermined period of time, the number of cells in "male" embryos must multiply at a faster rate. In accordance with the present teachings, processing video image data utilizing appropriately trained models for predicting respective sex can be utilized to determine the likelihood that the target embryo will produce a male offspring or will produce a female offspring. In this regard, even though biological sex can be considered binary, because a model trained for predicting "female" offspring indicates a 70% likelihood of producing a female offspring does not necessarily mean that a correspondingly trained model for predicting "male" offspring will indicate a 30% likelihood of producing a male offspring. To fit user expectation, however, an exemplary resolution is to predict both likelihoods, but only express a preference when one sex is predicted with a likelihood greater than 50% and the other sex is predicted with a likelihood less than 50%. Instances such as this help to illustrate the benefits and uses of the present technology, but also highlight the importance of human review and participation in embryo transfer decisions.

Typically, the videos of the blastocysts to be analyzed as described herein are taken in the "field," which is considered to be wherever the blastocyst is evaluated for transfer or preservation. In this context, "field" when referring to animals can be a veterinary clinic, barn, stock trailer and/or otherwise outdoors, for example. When considering humans, "field" typically refers to a fertility clinic and the like. Therefore, to avoid the need to transmit the video (which can comprise a data file of substantial size) to a remote analysis site, the trained model can be located on a local processor (computer, specialized chip, tablet, smart phone and the like) where the desired predictions are made. Alternatively, the data file can be transmitted to a host's remote site where the video file is processed, and resulting predictions transmitted back to the user in the field.

In practice, regardless of the field in which the blastocysts are collected, it is common for a plurality of blastocysts to be collected and suspended in nutritional media in a disposable receptacle such as a plastic or glass petri dish, organ culture dish or multi-well plate, as examples. Accordingly, a single video of a plurality of blastocysts in the receptacle can be taken and processed regarding each of the individual blastocysts for the characteristics which the model has been trained. An important aspect of the receptacle is that it has a transparent, substantially flat floor. An inverted microscope is exemplarily utilized to record a substantially distortion-free video of the blastocyst(s) from below the receptacle, through its clear, flat bottom surface. This creates a "goggle effect" and reduces "noise" in the sample from wave refraction caused by a rippling upper surface of the liquid media if observed from above. Exemplarily, an Iolight® brand compact inverted microscope has been utilized to record a video of the blastocyst(s). The magnification power is one-hundred and fifty times (150×), the frame speed is 10 fps, the pixel density is 2592×1944 and the microscope can connect to smartphones and/or tablets for sharing produced videos.

The presently disclosed technology enables the user to collect or receive secondary data obtained close in time to when the video from which the real-time digital video image data is derived was taken. In one configuration, the presently disclosed technology enables the user to perform a specific gravity assessment of the target embryo within one hour, or less, of taking the video of the target embryo. The specific gravity assessment used to obtain this example of secondary data is dependent upon a descent rate of the target embryo through embryo culture media. Secondary data collected and processed at the proximate time as real-time digital video image data can be indicative of the target embryo's viability, among other things.

Figure 2:
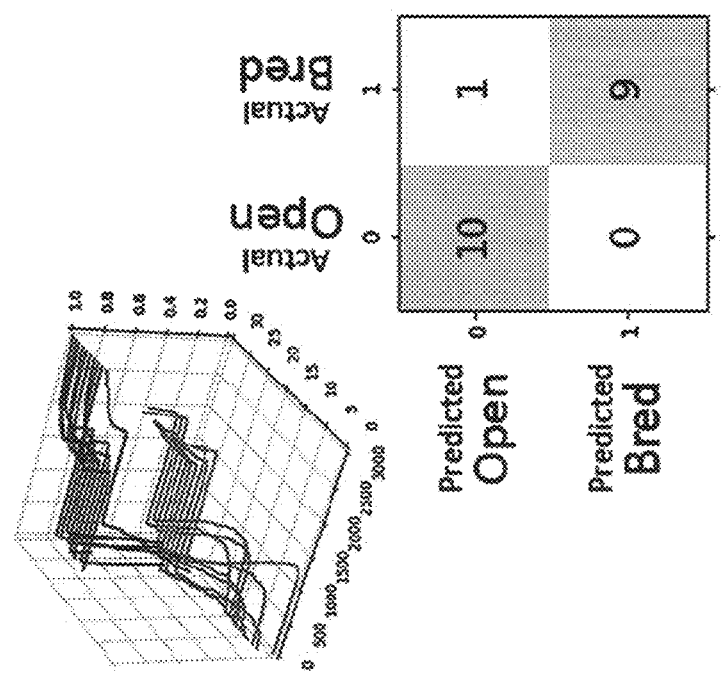
FIG. 2 depicts the outcome of video data processed using a model trained in accordance with the presently disclosed technology and which demonstrates: (1) a prediction accuracy rate of 91% for blastocysts that will not achieve pregnancy upon transfer and (2) a prediction accuracy rate of 100% for blastocysts that will achieve pregnancy upon transfer.
Figure 2:
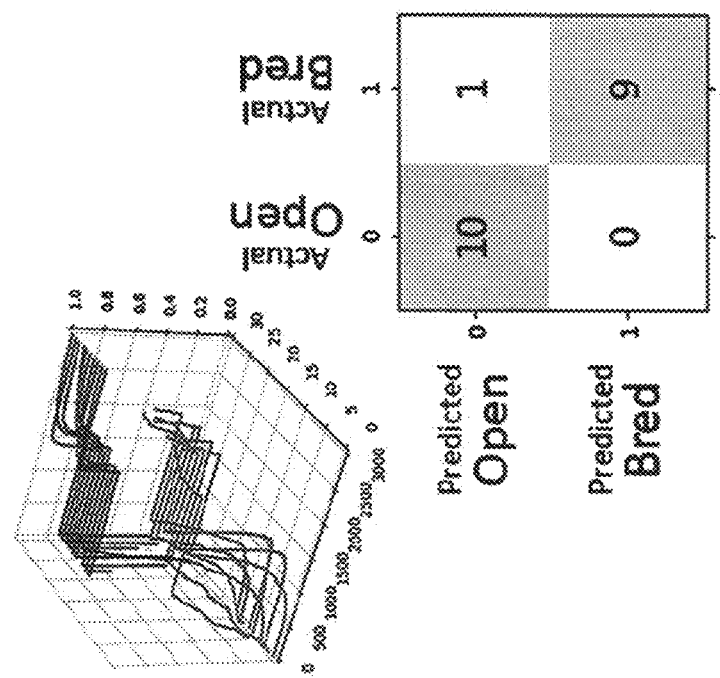

In one exemplary implementation illustrated in FIG. 2, a convolutional neural network model was utilized that is known to persons skilled in the art as Xception, or Xception71, and which is seventy-one layers deep and can consider approximately twenty-three million parameters. In this example, the model was trained on 256 videos of bovine embryos. Each video was thirty-five seconds in duration, taken at a frame-speed of fifteen frames-per-second, thereby rendering 134,400 (256×35×15) frames per processed video. Supervised training of the model was conducted with the 256 videos and each video had pregnancy data associated therewith indicative of whether a pregnancy (bred) occurred or not (open). Xception was used to process the training data and generate a predictive model. Thereafter, upon processing twenty new videos (n=20) using the trained model, ten of eleven (90.9%) videoed embryos were accurately predicted to NOT establish a pregnancy (open). The model accurately predicted nine of nine (100%) videoed embryos would establish a pregnancy (bred).

As an illustrative example, consider a dairy operation in which ten blastocysts have been flushed from a donor cow and deposited into a petri dish. There are only five available recipient cows, so the technician wishes to identify the five most viable, female-producing blastocysts. Video of the ten blastocysts is processed by a previously trained model that predicts and assigns, on an individual basis, a likelihood the particular blastocyst will produce a female calf. The comparable predictions (embryo outcome score) are then communicated back to the technician visually, or otherwise. In this way the technician can transfer the five blastocysts indicated to be most likely to produce female calves, in keeping with the goals of the dairy operation. In this way, desirable characteristics (or characteristics desired to be avoided) in mammalian offspring produced from a videoed embryo can be predicted for use in determining whether or not to transfer the particular embryo (blastocyst) into a recipient.

Turning now to the microscopic nature of the morphokinetic movements of embryos, not even under a microscope are such movements humanly discernible. For the purpose of revealing and sometimes accentuating certain aspects of embryo movement, Video Motion Magnification (VMM) has been optionally employed in accordance with the teachings of this description. VMM uses standard digital video image data sequences as input and applies spatial decomposition followed by temporal filtering of the frames. The resulting signal is then amplified to reveal the embryo's morphokinetic movement that has heretofore been unobservable. VMM is a relatively new technology that has been utilized in select physiological diagnostic applications, including remote, non-invasive measurement of patient heart rates and infants' respiration. In essence, this software can take videos of seemingly static scenes and cause micromotions captured therein to be rendered visually observable.

As has been well documented, developing embryos are undergoing mitosis at an exponential rate. Early in the development of this technology, it was hypothesized that applying video motion magnification to real-time video image data of embryos might allow operators to directly observe embryo development, embryo decay, and detect the presence of genetic abnormalities, among other things. However, it came to be appreciated that application of VMM to embryo video image data can be an enhancement in certain situations to the AI/ML model creation and utilization as disclosed herein. One of the most appealing aspects of VMM's processing of embryo video image data is its revelation of embryo movement that is easily displayed for human observation. Still further, when embryo video image data is VMM pre-processed and then used to create AI/ML models as otherwise (without VMM treatment) described herein, the ensuing embryo analysis and prediction can be enhanced.

In a study designed to determine the effectiveness of video motion magnification to amplify previously undetectable embryo morphokinetics, videos of bovine blastocysts were recorded at 150× magnification for two minutes by a licensed veterinarian using an inverted microscope. Once recorded, the videos were "filtered" using the VMM software, Lambda Vue, and movement of both the inner cell mass and zona pellucida became visually discernible when displayed. Protrusions, bulges, depressions, pulses and changes in embryo shape became observable. The presently disclosed technology is the first known to optionally amplify, and then analyze recorded micro-motions and the morphokinetics of embryo growth and development utilizing real time video, and without the use of time lapse imaging. In this study, ImageJ software developed by the National Institute of Health was utilized to take certain measurements of the embryos at specific locations and specific predetermined time intervals to study changes in embryo shape and size over short periods of time as described herein.

Even if not used for predictive purposes, amplification of the micro-motions of an embryo can be instructive (and comforting) to an operator as protrusions, bulges, depressions and shifts in the inner cell mass, trophectoderm and zona pellucida are made visible. Heretofore, it has been known, but not perceivable on a real-time basis, that blastomeres are actively dividing and increasing embryo mass until differentiation occurs at the blastocyst stage of development. Then, the blastomeres begin to arrange themselves into a distinct inner cell mass (developing fetus) and trophectoderm (developing placenta). In this regard, the human oocyte develops from a single cell into a blastocyst (~300 cells) in a span of five to six days. Previously, changes in blastomere arrangement, size, cell count and orientation were only demonstrated using time-lapse photography.

Cells grow, but they also die, and in the process undergo certain physical changes. When a cell dies, membrane proteins lose structural integrity and cannot osmoregulate their intracellular environment. Constituents from the external environment permeate into the cell through osmosis and intracellular constituents leak out of the cell. Non-viable embryos that include dead or dying cells absorb water as equilibrium is attempted. This occurs because water is attracted to the cell's intracellular environment and causes a low degree of cellular (embryo) swelling. After a cell has become non-viable for several hours, larger intracellular constituents such as salts and proteins begin to exit the cell and leak through the membrane proteins. This can be observed as cellular fragmentation and degrading. These properties cause physical changes in the appearance of the embryo which occur over time. However, the minute physical changes (with respect to both distance, rate and duration of motion) associated with both healthy embryo cellular growth and embryo cellular death are not humanly visible, even with the aid of a microscope up to 150× magnification. Applying video motion magnification filtering to embryo real-time video image data renders such motion visible to an operator and can optionally be included in the AI/ML modeling process described herein.

Figure 3:
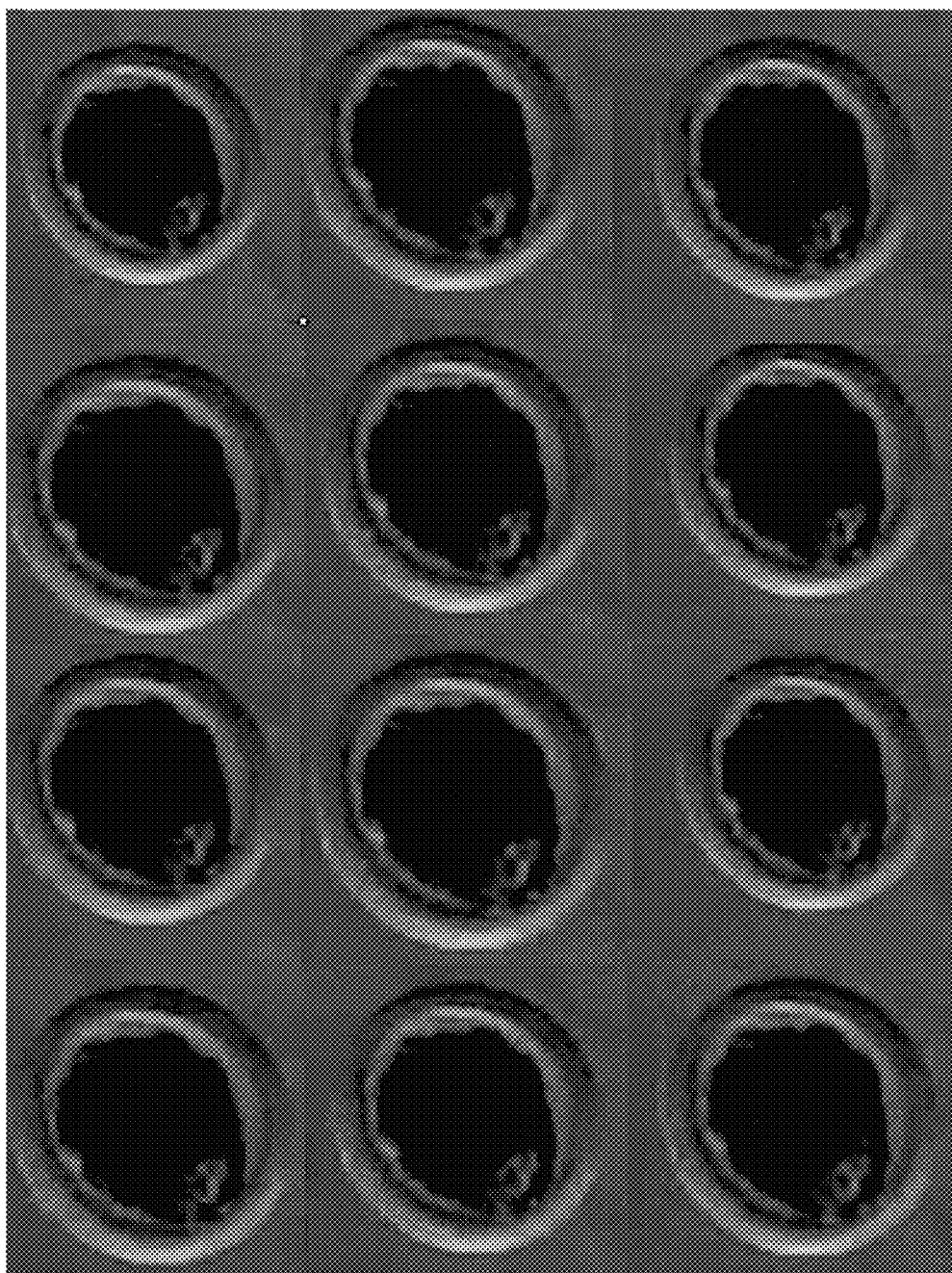
FIG. 3 depicts a series of 12 frames extracted from a video clip of a blastocyst using a microscope at 150× magnification.
Figure 4:
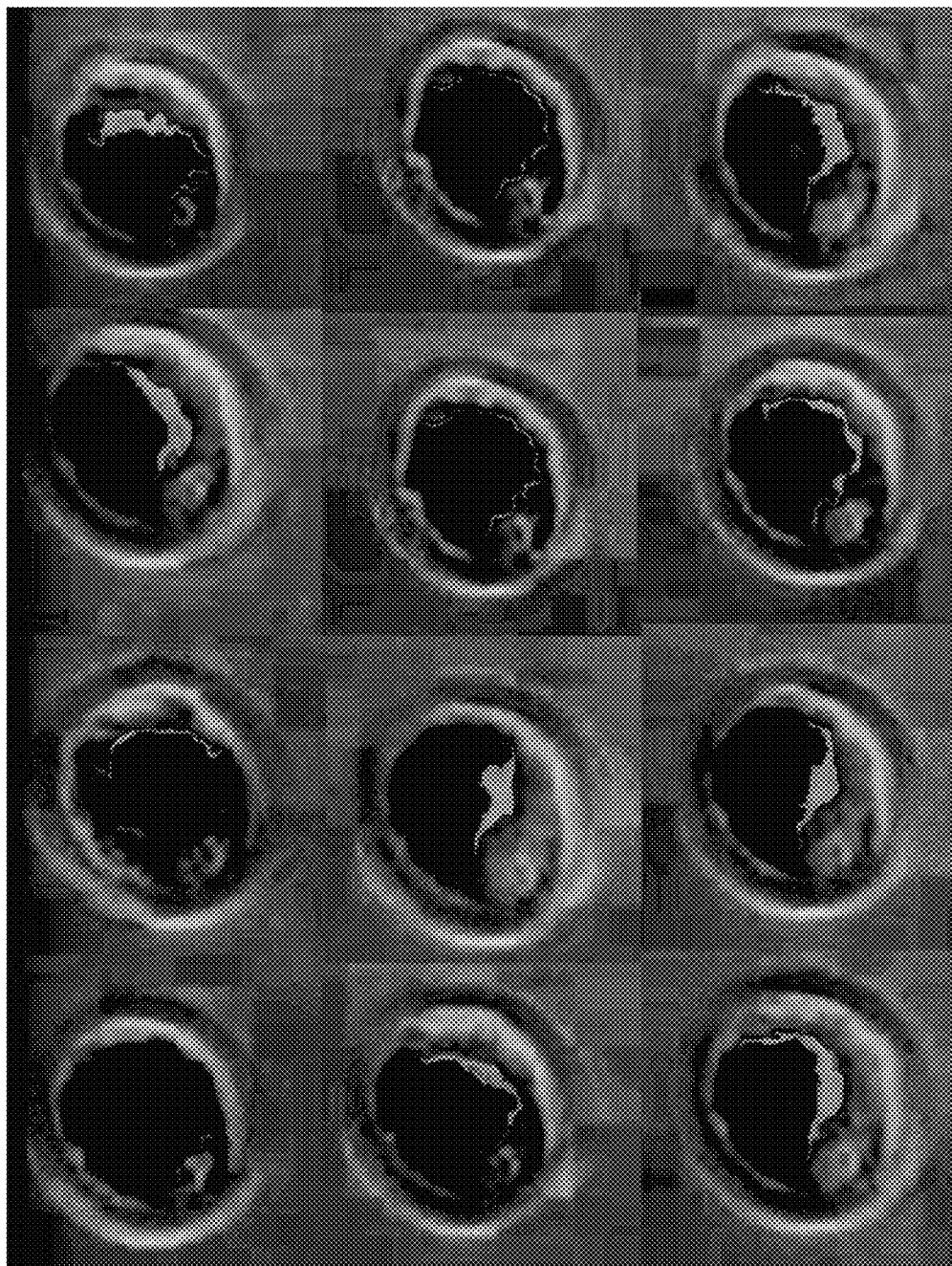
FIG. 4 depicts the same 12 frames of FIG. 3, but after being filtered using motion magnification software.

FIG. 3 depicts a series of twelve frames extracted from a video clip of a blastocyst (having a frame rate of 2 fps), without magnification (arranged left to right, top to bottom). Though it is known that blastocyst motion is occurring, it is not visible, even under the applied 150× microscope magnification. However, FIG. 4 depicts the same 12 frames after motion magnification, and the consecutive frames clearly depict motion in that the frames are progressively different, indicative and illustrative of the blastocyst's real-time motion. In at least one instance, video motion magnification has been used to detect embryo rate of growth to forecast cell count that is non-invasively predictive of embryo sex.

Another benefit of motion amplification is that the amplified image data can accentuate select motion characteristics being analyzed through vector weighting and other techniques (via computer vision, digital image processing or otherwise) during the training and model development stage, or afterward during utilization of the generated model for predictive purposes.

Figure 5:
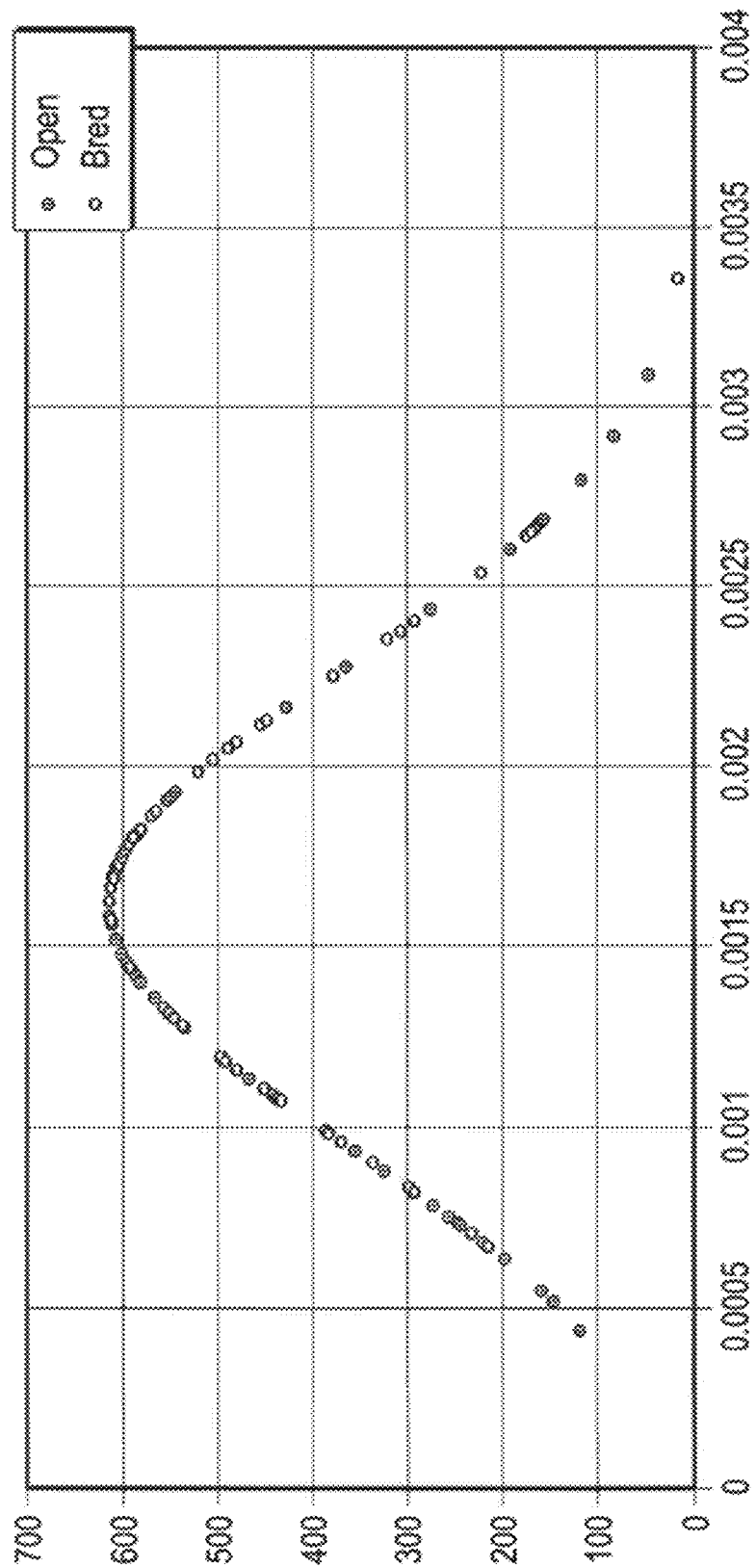
FIG. 5 is a graph showing that morphokinetic activity is predictive of a preimplantation embryo's likelihood to produce pregnancy.

In support of the discoveries disclosed herein regarding training and using AI/ML models to predict, among other things, embryo viability and certain offspring characteristics, reference is made to the disclosure of FIG. 5. Therein, a proxy for each of several embryo's morphokinetic activity has been quantified and plotted on the illustrative graph. For the quantification, a mean of average subzonal change was determined for each embryo, and which was considered to represent the embryo's morphokinetic activity. Each such value was divided by the particular embryo's inner cell mass area to calculate a standardized percent movement of that embryo, comparable with the other similarly "normalized" embryos. FIG. 5 represents a study in which the standardized percent morphokinetic activity values for each of 94 bovine embryos were plotted on the displayed graph. From the graph it is gleaned that twenty-four embryos (24/94=25%) had morphokinetic changes outside (some above, some below) of 2 standard deviations from the mean, which is signified by the left and right "tails" of the illustrative bell-shaped plot. Of those 24 embryos, 17 (17/24=70%) did not establish pregnancies ("open"); still further, these 17 embryos represent 18%=17/94 of the 94 total embryos. This is confirmatory in that it coincides with what has been found in practice and predicted by the instant models; that is, approximately 20% of grade-1 and grade-2 technician-assessed embryos, though otherwise expected, fail to produce a pregnancy upon transfer.

Figure 6:
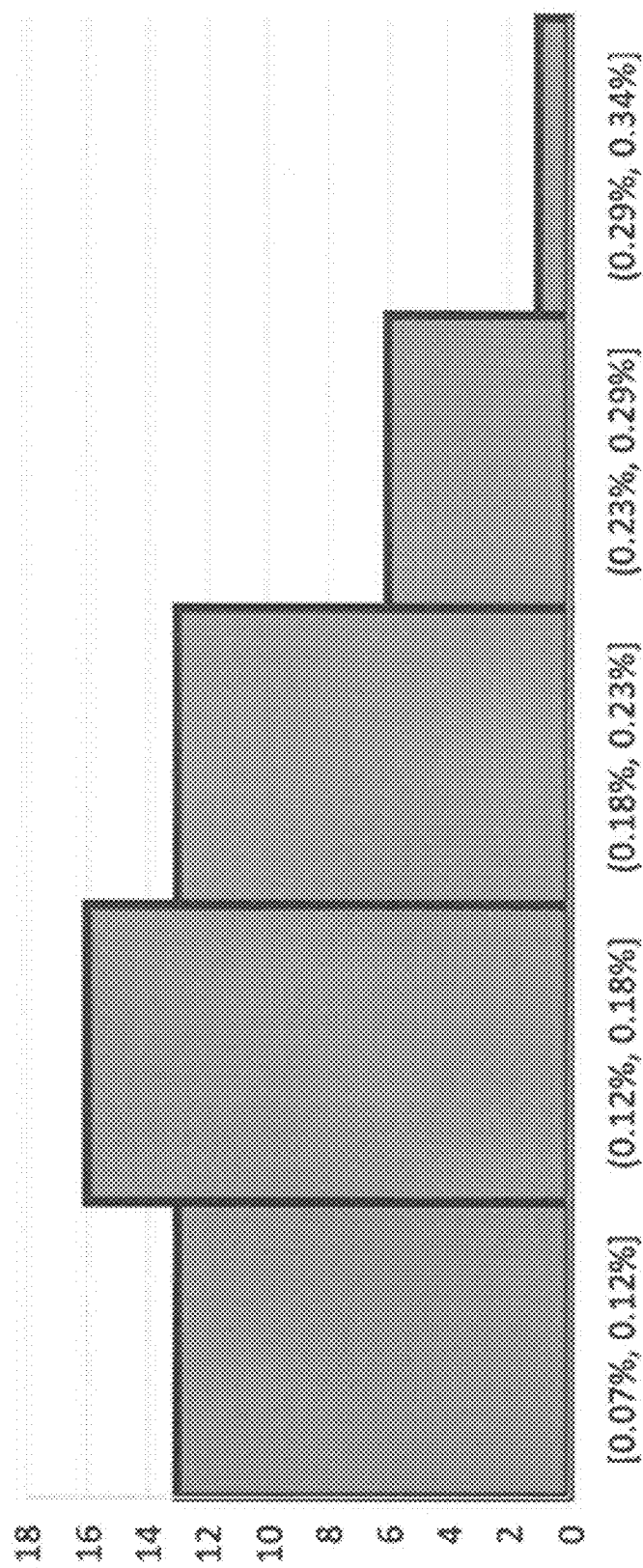
FIG. 6 is a histogram depicting morphokinetic patterns of embryos that produced pregnancy.

FIG. 6 is a histogram that depicts, out of the same 94 bovine embryos plotted in FIG. 5, the standardized percent morphokinetic activity values for the 50 (of the 94) bovine embryos that produced pregnancy. Of these 50 embryos, 42 (84%) demonstrated morphokinetic activity values ranging from 0.07%-0.23% (that is, taken from the left, the first three bars). However, the distribution of embryos across those first three bars—0.07%-0.12% {13 embryos}; 0.12%-0.18% {16 embryos} and 0.18%-0.23% {13 embryos}—were not statistically significant ($p>0.05$). Six embryos (12% of the 50 embryos that established pregnancies) demonstrated percent morphokinetic activity values of 0.23%-0.29% and one embryo (2% of the 50 embryos that established pregnancies) demonstrated a percent morphokinetic activity value of 0.29-0.34%. This is confirmatory of the position that embryos with hyperactive morphokinetic activity are less likely to produce pregnancy than those embryos having moderate morphokinetic activity, a position that has also been determined and predicted by the models of the present disclosure.

Figure 7:
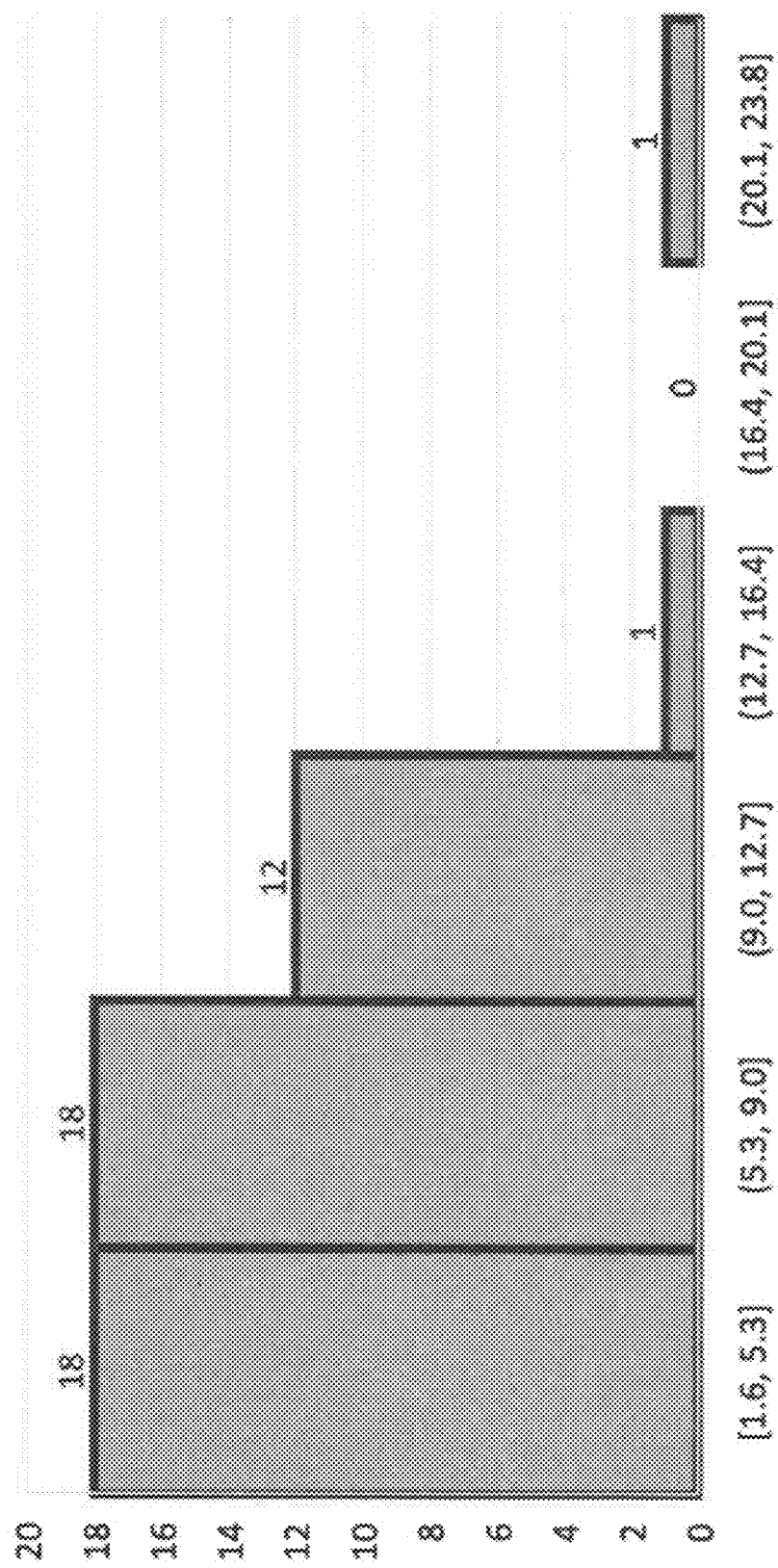
FIG. 7 is a histogram depicting the range of embryo movement within subzonal space as being an indicator of embryo competency for producing pregnancy.

The histogram of FIG. 7 illustrates and supports the proposition in this disclosure that determined inner cell mass range of motion within the subzonal space is indicative/predictive of the embryo's competence for establishing pregnancy. The histogram is based on measured radial distances of the gap spaces between the outer contours of the inner cell mass area and the zona pellucida at twelve indicated equal-spaced locations therearound every five seconds between 5 and 35 seconds (7 measurements) along the dashed lines depicted in FIGS. 8 and 9. For each of the 94 embryos, the measured amounts of motion over the 35 second period at each of the 12 locations were averaged for each of the 94 embryos that were transferred into recipients. The histogram of FIG. 7 depicts the 50 embryos that achieved pregnancy. Therein, it is revealed that embryos in the lower ranges of subzonal activity (bars toward the left) established pregnancies at a higher frequency than embryos with a high range of subzonal activity (bars toward the right) ($p<0.05$). Out of the 50 embryos, 48 (96%) demonstrated average ranges of motion between 1.6 um and 12.7 um, whereas only 2 out of the 50 embryos (4%) demonstrated a range of motion higher than 12.7 um.

Figure 8:
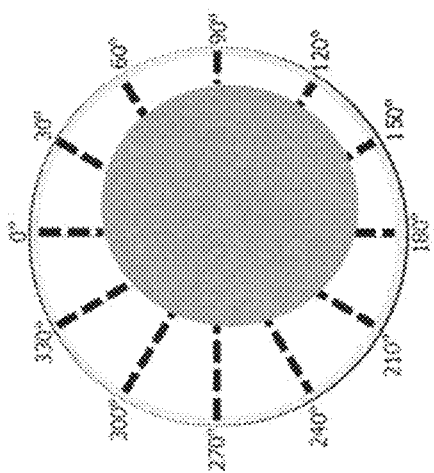
FIG. 8 illustrates components, area measurements and axial lines of measurement on a blastocyst that can be utilized to describe the blastocyst's morphokinetic activity.
Figure 8:
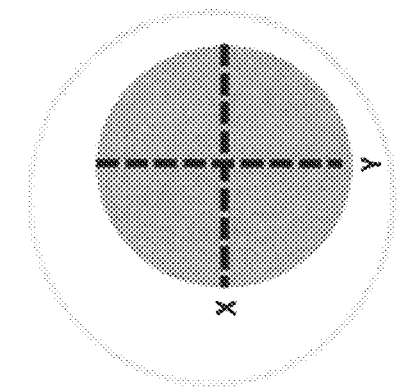
Figure 8:
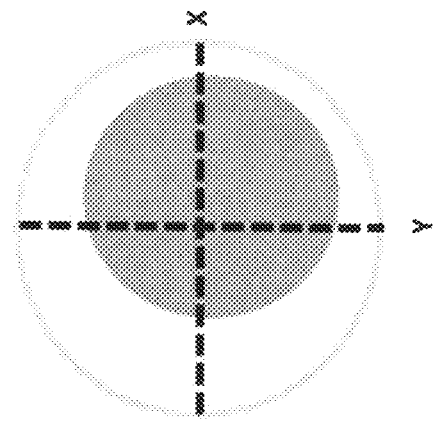
Figure 9:
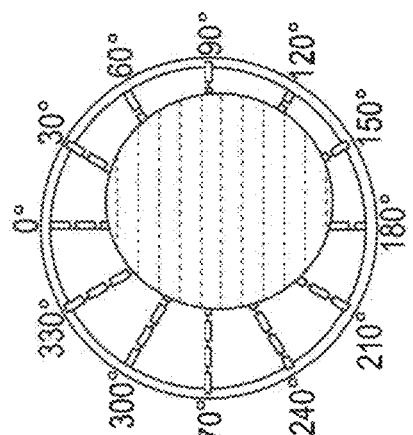
FIG. 9 superimposes lines of measure on an embryo for demonstrating movement of the inner cell mass within the zona pellucida of a blastocyst (an embryo) by assessing the varying distances therebetween.
Figure 9:
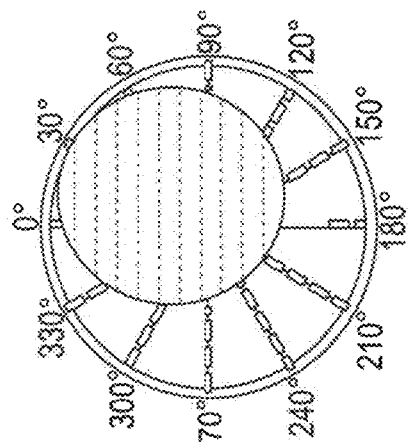
Figure 9:
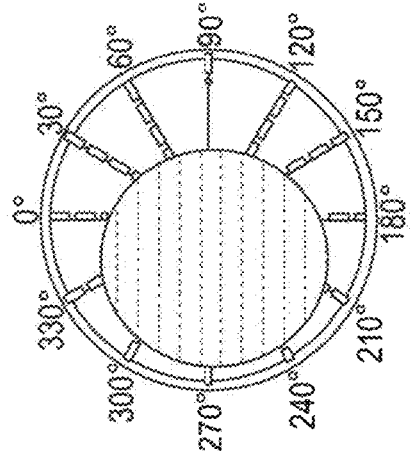
Figure 10:
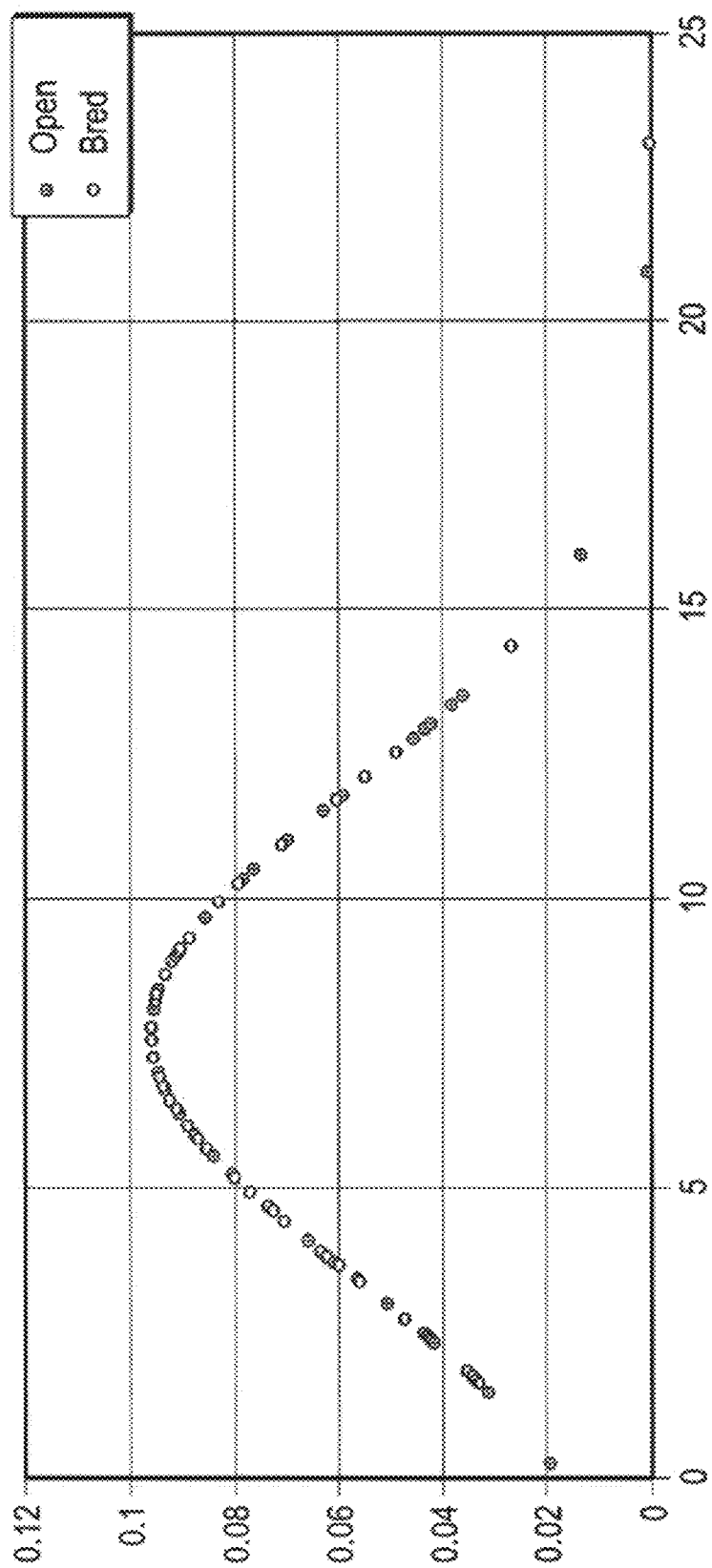
FIG. 10 is a graph showing that high morphokinetic activity is predictive of a preimplantation embryo's likelihood not to produce pregnancy.

FIG. 10 is a graph that depicts distances between the outer contours of the inner cell mass area and the zona pellucida of each of the 94 embryos measured at the specific 12 locations indicated in FIGS. 8 and 9 at five second intervals during a 35 second observatory period. The range of motion was calculated at each of the 12 locations over the 35 second duration and then averaged for each of the 94 embryos which were transferred into recipients. Nine of the 94 embryos (9.57%) demonstrated an average range of subzonal motion (activity) greater than 12.5 um, and seven of those nine embryos did not establish pregnancies, again indicating that embryos experiencing a high degree of subzonal activity are less likely to establish pregnancies than embryos experiencing a moderate range of motion.

In another study, bovine oocytes were fertilized in vivo by a licensed veterinarian. The embryos were flushed from the donor and placed in holding media. Two-minute video recordings were taken on an inverted microscope at 150× magnification. Confirmatory measurements were taken about each embryo using ImageJ Software. Among others, those measurements include: (1) Zona pellucida X axis diameter; (2) zona pellucida Y axis diameter; (3) mass X axis diameter; (4) mass Y axis diameter; (5) zona area; (6) mass area; (7) inner cell mass area and (8) rotational shift within the subzonal space. For each two-minute video, each of these measurements were made at the 0, 15, 30, 45, 60, 75, 90, 105 and 120 second time points. Immediately after their video was taken, each embryo was transferred into a recipient animal as a singleton (one embryo per recipient). Subsequent to this study, additional studies obtaining similar results have been conducted on embryo video clips that are 35 seconds long and were taken at ten frames per second (10 fps) prior to transfer into a recipient. Thereafter, pregnancy data, as outcome data, was obtained by trans-rectal ultrasound at forty days post transfer.

In still another study, 150 grade-1 and grade-2 embryos were flushed from beef cattle by a licensed veterinarian. Two-minute video recordings were captured from each embryo with an Iolight® inverted microscope at 150× in a standard culture of Vigro Holding Plus media. All embryos were transferred into eligible recipients. Videos were processed with Lambda Vue Video Motion Magnification Videoscope at 0.2-4 video frequency. Each amplified video was then assessed using ImageJ measuring software by taking measurements of the same embryo features at 15 second time intervals. The following measurements were made on each embryo, every 15 seconds: (1) Zona pellucida Y-axis diameter; (2) zona pelludica X-axis diameter; (3) mass Y-axis diameter; (4) mass X-Axis diameter; (5) zona pelludica area and (6) inner cell mass area and at twelve locations on the sub-zonal space as generally depicted in FIGS. 8 and 9. Observations were also made of bulges on the zona pellucida and bulges on the inner cell mass, when occurring.

In yet another trial, videos of embryos were obtained and amplified using video motion magnification. Y-axis diameter of the inner cellular mass was measured using ImageJ software (National Institute of Health) and scaled to represent units in microns. Measurements were obtained at five second intervals from 0 to 35 seconds. Quantifiable changes in embryo inner cell mass diameter were observed, demonstrating morphokinetic changes in short observatory periods. These were observed visually as bulges, depressions and protrusions in the inner cell mass over time. These changes infer predictive information pertaining to embryo health and viability based on the other findings described herein.

In a similar trial, videos of embryos were obtained and amplified using video motion magnification. Area of the inner cell mass was obtained using measurement tools available from ImageJ software (National Institute of Health) and scaled to represent units in microns. Measurements were obtained at five second intervals from 0 to 35 seconds. As before, quantifiable changes in inner cell mass area were observed, likewise demonstrating morphokinetic changes in short observatory periods. The measurements represent a 2-D area of the visible inner cell mass. It was observed that the cells were actively moving, likely due to mitosis and cellular division. It is believed that in some instances one cell mass overlapped another making the 2D area of the second cell mass appear to decrease, when it was not decreasing. The present technology demonstrates active development or cellular decay and does not depend on additive or subtractive trends as in time-lapse analysis. As revealed by the present technology, these cellular (embryo) changes evidence morphokinetic developmental characteristics that are in fact predictive of embryo health, viability, stress, and genetic characteristics, both inferior and superior compared to average or "normal".

This disclosure describes several different permutations of a computer-implemented method for predicting an embryo's outcome by processing video image data of the embryo. The method includes receiving image data derived from video of a target embryo taken at substantially real-time frame speed during an embryo observation period of time. The video contains recorded morphokinetic movement of the target embryo occurring during the embryo observation period of time and which is represented in the received image data. The received image data is processed using a model generated utilizing machine learning and correlated embryo outcome data.

In a further aspect, the disclosed method predicts a correlating embryo outcome for the target embryo. In this sense, the predicted "correlating outcome" is of the same nature as the "correlated outcome" used to train the model. For instance, if a model is trained on images (image data) known to be of cats (the "correlated outcome"), in most instances, that so-trained model will be used to analyze (process) images (image data) and predict the likelihood (probability) the analyzed image is of a cat (the "correlating outcome").

In one option, the present method predicts a likelihood the target embryo will produce a specific sex offspring. In accordance with this disclosure, a trained model can be used to make such a prediction. In an initial step, machine learning is used to train a model using image data from video of each of a number of embryos. For each embryo, it is known whether that embryo produced a male or female offspring and data representing that fact is paired to the corresponding video. In this sense, the corresponding male/female data is "correlated outcome data" to the respective videos. That is, the male/female "outcome data" is "correlated" with the respective videos. Machine learning is then utilized to analyze the paired data (video image data with its matched offspring sex data) and determine characteristics in the video image data that are indicative of male sex offspring and characteristics in the video image data that are indicative of female sex offspring. Thereafter, to predict the likely sex of a produced offspring of a particular target embryo, received image data from real-time video taken of that embryo is processed using the trained model. The model outputs a "correlating embryo outcome" which is a prediction of the likelihood the target embryo will produce a male sex offspring and/or a prediction of the likelihood the target embryo will produce a female sex offspring.

In general, the method described above for generating machine-learning-based models and utilizing such models to process data and make predictions therewith, applies to the other predictive scenarios described herein.

As further options, the disclosed method can predict: (i) a likelihood the target embryo will produce human male offspring; (ii) a likelihood the target embryo will produce human female offspring; (iii) a likelihood the target embryo will produce bovine male offspring; or (iv) a likelihood the target embryo will produce bovine female offspring.

In another option, the method predicts a likelihood of successful transfer of the target embryo into a recipient. In yet another option, the method predicts viability of the target embryo at the time of transfer. In still another option, the method predicts a likelihood the target embryo will produce a genetically inferior offspring compared to average or "normal". In another option, the method predicts a likelihood the target embryo will produce a genetically superior offspring compared to average or "normal".

According to this technology, a predicted embryo outcome of the target embryo can be communicated to the originator of the received image data thereby assisting in a decision whether to transfer the target embryo into a recipient.

In one option, the correlated embryo outcome data represents embryo transfers into recipients that established pregnancy. In another option, the correlated embryo outcome data represents embryo transfers into recipients that produced livebirth offspring. In still another option, the correlated embryo outcome data represents embryo transfers into recipients that produced livebirth male offspring. In yet another option, the correlated embryo outcome data represents embryo transfers into recipients that produced livebirth female offspring. In still another option, the correlated embryo outcome data represents embryo transfers into recipients that produced genetically inferior offspring compared to average or "normal". In even another option, the correlated embryo outcome data represents embryo transfers into recipients that produced genetically superior offspring compared to average or "normal".

In a further aspect, the method includes receiving outcome data indicative of whether successful transfer of the target embryo into a recipient occurred, where successful transfer is indicated by the target embryo producing pregnancy in the recipient. In another aspect, the method includes receiving outcome data indicative of whether successful transfer of the target embryo into a recipient occurred, where successful transfer is indicated by the target embryo producing livebirth offspring out of the recipient.

In one embodiment, the method includes utilizing a frame speed sufficiently fast to capture at least one individual embryo morphokinetic movement during the embryo observation period of time. In another embodiment, the method includes utilizing a speed sufficiently fast to capture a series of embryo morphokinetic movements during the embryo observation period of time. In one option, the method utilizes a frame speed at least as fast as fifteen frames per second. In another option, the method utilizes a frame speed of at least ten frames per second. In yet another option, the method utilizes a frame speed of at least two frames per second. In still another option, the method maintains substantially uniform frame speed during the embryo observation period of time.

The presently described technology includes selecting a duration of image data received and determining the length of time of the embryo observation period of time based there upon. In one option, the embryo observation period of time is less than two minutes. In another option, the embryo observation period of time is less than thirty seconds. In one aspect, the method includes selecting an embryo observation period of time of less than two minutes. In another aspect, the method includes selecting an embryo observation period of time of less than thirty seconds.

In one example, the presently described real-time video clips, from which the received image data is obtained, are taken using an inverted microscope camera from a perspective below the target embryo. In another example, the video from which the received image data is obtained is taken using an inverted microscope camera from a perspective below and through a petri dish containing the target embryo, and in which the bottom floor of the petri dish is substantially flat and clear enabling the video of the target embryo to be optically accurate. In yet another example, the video from which the received image data is obtained is taken using a smartphone camera. In still another example, the camera is directly connected to a circuit board of an inclusive platform.

The present disclosure describes a method of receiving, from the same video, image data of each of a plurality of target embryos. In one embodiment, the method includes processing the image data for each of the plurality of target embryos utilizing the model and predicting an embryo outcome score for each of the plurality of target embryos. In accordance with this embodiment, the method includes communicating the predicted embryo outcome score of each of a plurality of the target embryos to an originator of the received image data, or otherwise user of the system, thereby assisting a decision of which embryos to transfer. Another embodiment includes communicating a ranking of the predicted embryo outcome scores to an originator of the received image data thereby assisting a decision of which embryos to transfer. In another embodiment, the method includes transmitting display data to a display observable by an originator of the received image data that causes ranked embryo outcome scores to be displayed in a spatial arrangement on the display that corresponds to an existing spatial arrangement of the target embryos.

The present technology facilitates a method of amplifying at least a portion of image data from within the received image data that represents morphokinetic movement of the target embryo. In one embodiment, the morphokinetic movement of the target embryo is humanly imperceptible at 150× magnification. In another embodiment, the method utilizes Eulerian video magnification to amplify the portion of image data from within the received image data that represents morphokinetic movement of the target embryo. In a further embodiment, the method utilizes the amplified data representing the morphokinetic movement of the target embryo to enable display of a moving image of the target embryo in which the movement is humanly perceptible.

In one aspect, at least one characteristic of the target embryo evidenced in the received image data is elasticity of the embryo's outer wall.

The present disclosure includes the method of receiving secondary data indicative of the target embryo's viability derived from a specific gravity assessment made of the embryo proximate in time to when the video from which the received image data is obtained was taken. In one option, the specific gravity assessment is made of the target embryo within one hour of taking the video of the target embryo. In another option, the specific gravity assessment is dependent upon a descent rate of the target embryo through embryo culture media.

In one embodiment, the method uses machine learning that comprises utilization of an artificial neural network.

In another aspect, the present disclosure describes a system containing one or more processors and a computer-readable medium, instructions stored within, which when executed by the one or more processors, cause the one or more processors to predict an embryo outcome by processing video image data of an embryo. The method includes receiving image data derived from video of a target embryo taken at substantially real-time frame speed during an embryo observation period of time. The video's resolution is sufficient (high enough) to record and does record morphokinetic movement of the target embryo occurring during the embryo observation period of time. The movement is represented in the received image data and the received image data is processed using a model generated utilizing machine learning and correlated embryo outcome data.

In still another aspect, the present disclosure describes a non-transitory computer-readable storage medium containing computer-readable instructions, which when executed by a computing system, cause the computing system to predict an embryo outcome by processing video image data of an embryo. The method includes receiving image data derived from video of a target embryo taken at substantially real-time frame speed during an embryo observation period of time. The video's resolution is sufficient (high enough) to record and does record morphokinetic movement of the target embryo occurring during the embryo observation period of time. The movement is represented in the received image data. The received image data is processed using a model generated utilizing machine learning and correlated embryo outcome data.

General Description of AI/ML and Exemplary System Configuration(s)

The disclosure set forth below provides general description of various configurations of the subject technology and is not intended to represent the only configurations in which the subject technology can be practiced. The appended drawings are incorporated herein and constitute a part of this specification. This description includes details for the purpose of providing a more thorough understanding of the subject technology. However, the subject technology is not limited to the specific details set forth therein and may be practiced with or without these details. In some instances, structures and components are shown in block diagram form so as to avoid obscuring the concepts of the subject technology.

Figure 11:
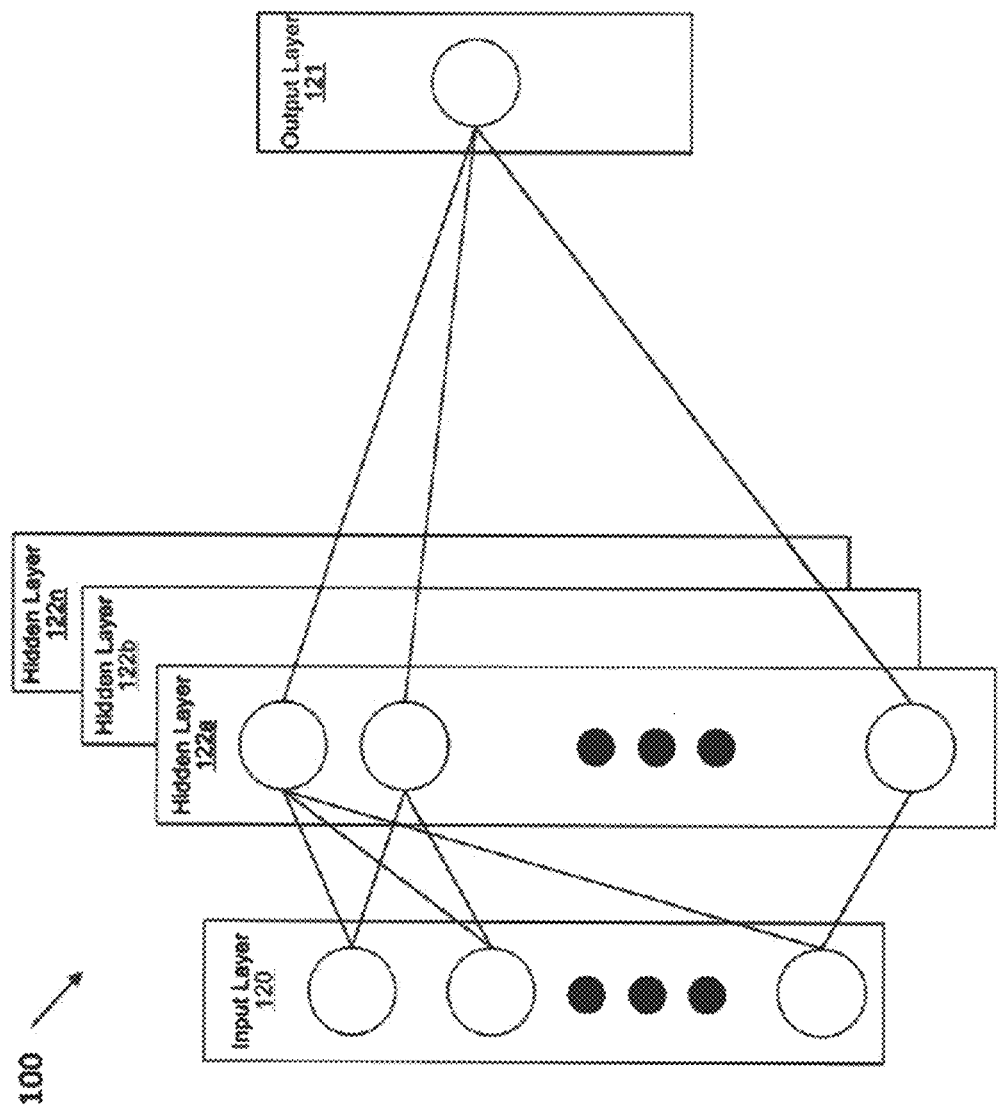
FIG. 11 is a schematic of an exemplary deep learning neural network useable for presently disclosed AI/ML model training, model generation and video image data processing using the generated models for predicting embryo traits and produced offspring characteristics.

The disclosure now turns to additional discussion of models that can be used in the environments and techniques described herein. Specifically, FIG. 11 is an illustrative example of a deep learning neural network 100. These networks are referred to as "neural" networks because they reflect the behavior of the human brain. These neural networks, also referred to as artificial neural networks (ANNs) and/or simulated neural networks (SNNs), are subsets of machine learning (ML). The network has an input layer 120 that is configured to receive input data, which in the present case is the video image data of embryos. The neural network 100 includes multiple hidden layers 122a, 122b, through 122n. The hidden layers 122a, 122b, through 122n include "n" number of hidden layers, where "n" is an integer greater than or equal to one. The number of hidden layers can be made to include as many layers as needed for the given application. The neural network 100 further includes an output layer 121 that provides an output resulting from the processing performed by the hidden layers 122a, 122b, through 122n. It is the presence of the multiple hidden layers that gives rise to the "deep learning" description.

The neural network 100 is a multi-layer neural network of interconnected nodes. Each node can represent a piece of information. Information associated with the nodes is shared among the different layers and each layer retains information as information is processed. In some cases, the neural network 100 can include a feed-forward network, in which case there are no feedback connections where outputs of the network are fed back into itself. In some cases, the neural network 100 can include a recurrent neural network, which can have loops that allow information to be carried across nodes while reading in input.

Information can be exchanged between nodes through node-to-node interconnections between the various layers. Nodes of the input layer 120 can activate a set of nodes in the first hidden layer 122a. For example, as shown, each of the input nodes of the input layer 120 is connected to each of the nodes of the first hidden layer 122a. The nodes of the first hidden layer 122a can transform the information of each input node by applying activation functions to the input node information. The information derived from the transformation can then be passed to and can activate the nodes of the next hidden layer 122b, which can perform their own designated functions. Example functions include convolutional, up-sampling, data transformation, and/or any other suitable functions. The output of the hidden layer 122b can then activate nodes of the next hidden layer, and so on. The output of the last hidden layer 122n can activate one or more nodes of the output layer 121, at which an output is provided. In some cases, while nodes in the neural network 100 are shown as having multiple output lines, a node can have a single output and all lines shown as being output from a node represent the same output value.

In some cases, each node or interconnection between nodes can have a weight that is a set of parameters derived from the training of the neural network 100. Once the neural network 100 is trained, it can be referred to as a trained neural network, which can be used to classify one or more activities. For example, an interconnection between nodes can represent a piece of information learned about the interconnected nodes. The interconnection can have a tunable numeric weight that can be tuned (e.g., based on a training dataset), allowing the neural network 100 to be adaptive to inputs and able to learn as more and more data is processed.

The neural network 100 can be pre-trained to process the features from the data in the input layer 120 using the different hidden layers 122a, 122b, through 122n in order to provide the output through the output layer 121.

In some cases, the neural network 100 can adjust the weights of the nodes using a training process called backpropagation. As noted above, a backpropagation process can include a forward pass, a loss function, a backward pass, and a weight update. The forward pass, loss function, backward pass, and parameter update is performed for one training iteration. The process can be repeated for a certain number of iterations for each set of training data until the neural network 100 is trained well enough so that the weights of the layers are accurately tuned.

In general, and as noted above, for a first training iteration for the neural network 100, the output will likely include values that do not give preference to any particular class due to the weights being randomly selected at initialization. For example, if the output is a vector with probabilities that the object includes different classes, the probability value for each of the different classes may be equal or at least very similar (e.g., for ten possible classes, each class may have a probability value of 0.1). With the initial weights, the neural network 100 is unable to determine low level features and thus cannot make an accurate determination of what the classification of the object might be. A loss function can be used to analyze error in the output. Any suitable loss function definition can be used, such as a Cross-Entropy loss. Another example of a loss function includes the mean squared error (MSE), defined as $E\_total=\Sigma(\frac{1}{2}(target-output)^2)$. The loss can be set to be equal to the value of $E\_total$.

Generally, a goal of training is to minimize the amount of loss so that the predicted output is the same as the training label. The neural network 100 can perform a backward pass by determining which inputs (weights) most contributed to the loss of the network, and can adjust the weights so that the loss decreases and is eventually minimized. A derivative of the loss with respect to the weights (denoted as dL/dW, where W are the weights at a particular layer) can be computed to determine the weights that contributed most to the loss of the network. After the derivative is computed, a weight update can be performed by updating all the weights of the filters. For example, the weights can be updated so that they change in the opposite direction of the gradient. The weight update can be denoted as $w=w\_i-\eta\ dL/dW$, where w denotes a weight, $w\_i$ denotes the initial weight, and $\eta$ denotes a learning rate. The learning rate can be set to any suitable value, with a high learning rate including larger weight updates and a lower value indicating smaller weight updates.

The neural network 100 can include any suitable deep network. One example includes a convolutional neural network (CNN), which includes an input layer and an output layer, with multiple hidden layers between the input and out layers. The hidden layers of a CNN include a series of convolutional, nonlinear, pooling (for downsampling), and fully connected layers. The neural network 100 can include any other deep network other than a CNN, such as an autoencoder, a deep belief nets (DBNs), a Recurrent Neural Networks (RNNs), among others.

As understood by those persons skilled in these arts, machine-learning based classification techniques can vary depending on the desired implementation. For example, machine-learning classification schemes can utilize one or more of the following, alone or in combination: hidden Markov models; recurrent neural networks; convolutional neural networks (CNNs); deep learning; Bayesian symbolic methods; generative adversarial networks (GANs); support vector machines; image registration methods; applicable rule-based system. Where regression algorithms are used, they may include but are not limited to: a Stochastic Gradient Descent Regressor, and/or a Passive Aggressive Regressor, and the like.

Machine learning classification models can also be based on clustering algorithms (e.g., a Mini-batch K-means clustering algorithm), a recommendation algorithm (e.g., a Miniwise Hashing algorithm, or Euclidean Locality-Sensitive Hashing (LSH) algorithm), and/or an anomaly detection algorithm, such as a Local outlier factor. Additionally, machine-learning models can employ a dimensionality reduction approach, such as, one or more of: a Mini-batch Dictionary Learning algorithm, an Incremental Principal Component Analysis (PCA) algorithm, a Latent Dirichlet Allocation algorithm, and/or a Mini-batch K-means algorithm and the like.

Figure 12:
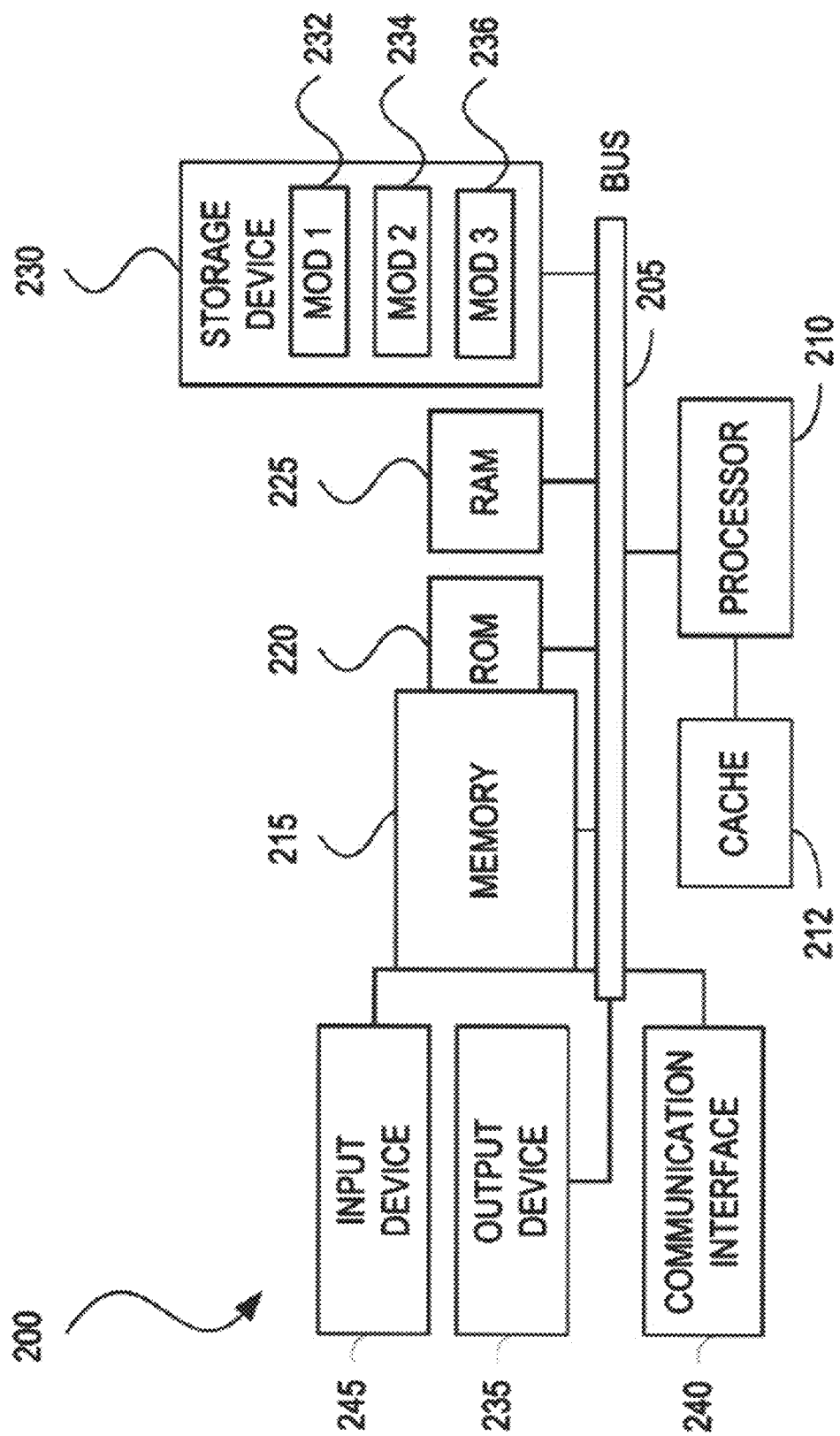
FIG. 12 depicts an exemplary processor-based computing system suitable for use as a platform for executing certain routines of the presently disclosed AI/ML modeling.

The disclosure now turns to FIG. 12 which illustrates an example of a processor-based computing system 200 wherein the components of the system are in electrical communication with each other using a system bus 205. The computing system 200 can include a processing unit (CPU or processor) 210 and a system bus 205 that may couple various system components including the system memory 215, such as read only memory (ROM) 220 and random-access memory (RAM) 225, to the processor 210. The computing system 200 can include a cache 212 of high-speed memory connected directly with, in close proximity to, or integrated as part of the processor 210. The computing system 200 can copy data from the memory 215, ROM 220, RAM 225, and/or storage device 230 to the cache 212 for quick access by the processor 210. In this way, the cache 212 can provide a performance boost that avoids processor delays while waiting for data. These and other modules can control the processor 210 to perform various actions. Other system memory 215 may be available for use as well. The memory 215 can include multiple different types of memory with different performance characteristics. The processor 210 can include any general-purpose processor and a hardware module or software module, such as module 1 232, module 2 234, and module 3 236 stored in the storage device 230, configured to control the processor 210 as well as a special-purpose processor where software instructions are incorporated into the actual processor design. The processor 210 may essentially be a completely self-contained computing system, containing multiple cores or processors, a system bus, memory controller, cache, etc. A multi-core processor may be symmetric or asymmetric.

To enable user interaction with the computing system 200, an input device 245 can represent any number of input mechanisms, such as a microphone for speech, a touch-protected screen for gesture or graphical input, keyboard, mouse, motion input, speech and so forth. An output device 235 can also be one or more of a number of output mechanisms known to those of skill in the art. In some instances, multimodal systems can enable a user to provide multiple types of input to communicate with the computing system 200. The communications interface 240 can govern and manage the user input and system output. There may be no restriction on operating on any particular hardware arrangement and therefore the basic features here may easily be substituted for improved hardware or firmware arrangements as they are developed.

The storage device 230 can be a non-volatile memory and can be a hard disk or other types of computer readable media which can store data that are accessible by a computer, such as magnetic cassettes, flash memory cards, solid state memory devices, digital versatile disks, cartridges, random access memory, read only memory, and hybrids thereof.

As discussed above, the storage device 230 can include the software modules 232, 234, 236 for controlling the processor 210. Other hardware or software modules are contemplated. The storage device 230 can be connected to the system bus 205. In some embodiments, a hardware module that performs a particular function can include a software component stored in a computer-readable medium in connection with the necessary hardware components, such as the processor 210, system bus 205, output device 235, and so forth, to carry out the function. For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general-purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

What is claimed:

1. A computer-implemented method for predicting an embryo outcome by processing video image data of an embryo, the method comprising:

obtaining image data derived from video of a target embryo taken at real-time frame speed during an embryo observation period of time of less than two minutes, wherein said video contains recorded morphokinetic movement of the target embryo occurring during the embryo observation period of time and wherein said recorded morphokinetic movement is represented in the image data, and processing the image data using a model generated utilizing machine learning and correlated embryo outcome data and wherein the image data is derived from video taken while maintaining substantially uniform frame speed during the embryo observation period of time.

2. A system comprising:

one or more processors; and a computer-readable medium comprising instructions stored therein, which when executed by the one or more processors, cause the one or more processors to:

predict an embryo outcome by processing video image data of the embryo, said prediction comprising:

receiving image data derived from video of a target embryo taken at real-time frame speed during an embryo observation period of time of less than two minutes, wherein said video contains recorded morphokinetic movement of the target embryo occurring during the embryo observation period of time and wherein said recorded morphokinetic movement is represented in the image data; and processing the image data using a model generated utilizing machine learning and correlated embryo outcome data.

3. The system of claim 2, further comprising: predicting a likelihood of successful transfer of the target embryo into a recipient.

4. The system of claim 2, further comprising: predicting viability of the target embryo.

5. The system of claim 2, wherein the correlated embryo outcome data represents embryo transfers into recipients that established pregnancy.

6. The system of claim 2, wherein the correlated embryo outcome data represents embryo transfers into recipients that produced livebirth offspring.

7. The system of claim 2, further comprising: obtaining outcome data indicative of whether successful transfer of the target embryo into a recipient occurred, wherein successful transfer is indicated by the target embryo producing pregnancy in the recipient.

8. The system of claim 2, further comprising: obtaining outcome data indicative of whether successful transfer of the target embryo into a recipient occurred, wherein successful transfer is indicated by the target embryo producing livebirth offspring out of the recipient.

9. The system of claim 2, wherein the image data is derived from video having a frame speed at least as fast as two frames per second.

10. The system of claim 2, further comprising: wherein the duration of the embryo observation period of time is less than thirty seconds.

11. A non-transitory computer-readable storage medium comprising computer-readable instructions, which when executed by a computing system, cause the computing system to:
   predict an embryo outcome by processing video image data of an embryo, said prediction comprising:
      receiving image data derived from video of a target embryo taken at real-time frame speed during an embryo observation period of time of less than two minutes, wherein said video contains recorded morphokinetic movement of the target embryo occurring during the embryo observation period of time and wherein said recorded morphokinetic movement is represented in the image data; and
      processing the image data using a model generated utilizing machine learning and correlated embryo outcome data.

12. The storage medium of claim 11, further comprising: predicting a likelihood of successful transfer of the target embryo into a recipient.

13. The storage medium of claim 11, further comprising: predicting viability of the target embryo.

14. The storage medium of claim 11, wherein the correlated embryo outcome data represents embryo transfers into recipients that produced livebirth offspring.

15. The storage medium of claim 11, further comprising: obtaining outcome data indicative of whether successful transfer of the target embryo into a recipient occurred, wherein successful transfer is indicated by the target embryo producing pregnancy in the recipient.

16. The storage medium of claim 11, further comprising: obtaining outcome data indicative of whether successful transfer of the target embryo into a recipient occurred, wherein successful transfer is indicated by the target embryo producing livebirth offspring out of the recipient.

17. The storage medium of claim 11, wherein the image data is derived from video having a frame speed at least as fast as two frames per second.

18. The storage medium of claim 11, wherein the image data is derived from video having a frame speed at least as fast as fifteen frames per second.

19. The storage medium of claim 11, wherein the duration of the embryo observation period of time is less than thirty seconds.

20. A computer-implemented method for predicting an embryo outcome by processing video image data of an embryo, the method comprising:
   obtaining image data derived from video of a target embryo taken at real-time frame speed during an embryo observation period of time of less than two minutes, wherein said video contains recorded morphokinetic movement of the target embryo occurring during the embryo observation period of time and wherein said recorded morphokinetic movement is represented in the image data; and
   processing the image data using a model generated utilizing machine learning and correlated embryo outcome data.

21. The method of claim 20, further comprising: processing the image data using a model generated utilizing machine learning and correlated embryo outcome data.

22. The method of claim 20, further comprising: predicting a likelihood of successful transfer of the target embryo into a recipient.

23. The method of claim 20, further comprising: predicting viability of the target embryo.

24. The method of claim 20, further comprising: communicating a predicted embryo outcome of the target embryo to an originator of the obtained image data.

25. The method of claim 20, wherein the correlated embryo outcome data represents embryo transfers into recipients that established pregnancy.

26. The method of claim 20, wherein the correlated embryo outcome data represents embryo transfers into recipients that produced livebirth offspring.

27. The method of claim 20, further comprising: obtaining outcome data indicative of whether successful transfer of the target embryo into a recipient occurred, wherein successful transfer is indicated by the target embryo producing pregnancy in the recipient.

28. The method of claim 20, further comprising: obtaining outcome data indicative of whether successful transfer of the target embryo into a recipient occurred, wherein successful transfer is indicated by the target embryo producing livebirth offspring out of the recipient.

29. The method of claim 20, wherein the duration of the embryo observation period of time is less than thirty seconds.

30. The method of claim 20, wherein the image data is derived from video having a frame speed at least as fast as two frames per second.

* * * * *